(12) United States Patent
Shaikh et al.

(10) Patent No.: US 12,124,920 B2
(45) Date of Patent: Oct. 22, 2024

(54) EVENT STATUS APPARATUSES AND RELATED DEVICES, SYSTEMS, AND METHODS

(71) Applicant: Lupin Limited, Mumbai (IN)

(72) Inventors: Imran Shaikh, Coral Springs, FL (US); Mukul Dalvi, Coral Springs, FL (US); Xian-Ming Zeng, Coral Springs, FL (US); David Schaller, Chicago, IL (US); Cameron Alberg, Chicago, IL (US)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 17/768,430

(22) PCT Filed: Oct. 3, 2020

(86) PCT No.: PCT/IB2020/059301
§ 371 (c)(1),
(2) Date: Apr. 12, 2022

(87) PCT Pub. No.: WO2021/064700
PCT Pub. Date: Apr. 8, 2021

(65) Prior Publication Data
US 2024/0119250 A1    Apr. 11, 2024

Related U.S. Application Data

(60) Provisional application No. 62/913,982, filed on Oct. 11, 2019, provisional application No. 62/910,551, filed on Oct. 4, 2019.

(51) Int. Cl.
*A61M 15/00* (2006.01)
*G06M 1/04* (2006.01)
(Continued)

(52) U.S. Cl.
CPC ........ *G06M 1/248* (2013.01); *A61M 15/0075* (2014.02); *A61M 15/009* (2013.01);
(Continued)

(58) Field of Classification Search
CPC ...... G06M 1/248; G06M 1/045; G06M 1/083; G06M 1/04; G06M 1/08; A61M 15/0075;
(Continued)

(56) References Cited

U.S. PATENT DOCUMENTS 5,988,496 A    11/1999  Bruna
6,142,339 A *  11/2000  Blacker ............. A61M 15/0075
                                                        222/38
(Continued)

FOREIGN PATENT DOCUMENTS

DE    102006040194 A1    3/2008
EP        0269496 A2     6/1988
(Continued)

OTHER PUBLICATIONS

PCT Search Report & Written Opinion dated Jan. 25, 2021, Application No. PCT/IB2020/059301.

*Primary Examiner* — Frederick C Nicolas
(74) *Attorney, Agent, or Firm* — The Dobrusin Law Firm, P.C.

(57) ABSTRACT

Provided herein are new devices for indicating the status of events, such as the number of relevant events that are remaining and/or that have already occurred up to the present moment and to related devices, systems, and methods. In some aspects, the event-related indicator devices of the invention are used within larger dispensing devices or systems, e.g., to provide the status of administration of a substance contained therein (e.g., a drug). In an exemplary embodiment, the indicator devices find particular utility within medicament dispensers, such as metered dose inhal- (Continued)

ers, to provide a visual indication of the status of doses having been or remaining to be administered.

35 Claims, 9 Drawing Sheets

(51) Int. Cl.
  *G06M 1/08* (2006.01)
  *G06M 1/24* (2006.01)
  *A61M 16/00* (2006.01)

(52) U.S. Cl.
  CPC .............. *G06M 1/04* (2013.01); *G06M 1/045* (2013.01); *G06M 1/08* (2013.01); *G06M 1/083* (2013.01); *A61M 2016/0015* (2013.01); *A61M 2205/3306* (2013.01); *A61M 2205/3368* (2013.01); *A61M 2205/3375* (2013.01); *A61M 2205/583* (2013.01); *A61M 2205/584* (2013.01)

(58) Field of Classification Search
  CPC .. A61M 2016/0015; A61M 2205/3306; A61M 2205/3368; A61M 2205/3375; A61M 2205/583; A61M 2205/584; A61M 15/009
  See application file for complete search history.

(56) References Cited

U.S. PATENT DOCUMENTS

| | | | |
|---|---|---|---|
| 6,360,739 B1* | 3/2002 | Rand | A61P 11/08 |
| | | | 128/200.14 |
| 8,113,199 B2 | 2/2012 | Augustyn et al. | |
| 8,820,318 B2* | 9/2014 | Crosby | A61M 15/009 |
| | | | 128/200.14 |
| 9,089,661 B2 | 7/2015 | Stuart et al. | |
| 9,125,999 B2* | 9/2015 | Rolfs | A61M 15/0025 |
| 9,517,314 B2* | 12/2016 | Hately | A61M 15/0075 |
| 11,037,047 B2* | 6/2021 | Christie | G06M 1/16 |

FOREIGN PATENT DOCUMENTS

| | | |
|---|---|---|
| GB | 2502791 A | 12/2013 |
| WO | 01/31578 A1 | 5/2001 |
| WO | 2005/060535 A2 | 7/2005 |
| WO | 2005/079727 A2 | 9/2005 |
| WO | 2007/124406 A2 | 11/2007 |

* cited by examiner

EVENT STATUS APPARATUSES AND RELATED DEVICES, SYSTEMS, AND METHODS

CROSS REFERENCE TO RELATED APPLICATIONS

This application is being filed as a PCT International patent application, and claims priority to a U.S. Provisional Applications Nos. 62/910,551 and 62/913,982 filed on Oct. 4, 2019 and Oct. 11, 2019 respectively. The entirety of the aforementioned application is hereby incorporated herein by reference.

FIELD OF THE INVENTION

The present invention relates to event-related status devices/components capable of indicating to a user the status of events, such as the number of relevant events that are remaining and/or that have already occurred to the present moment and to related devices, systems, and methods of using or making such devices and systems. In an exemplary embodiment, the invention relates to new and useful dose counters for use in, e.g., medicine dose-dispensing devices and associated components, devices, and methods.

BACKGROUND OF THE INVENTION

Event status indicators find application across a diverse group of fields ranging from mechanical event counters such as those used in games, such as baseball to register balls and strikes, to event counters used in computers and electronics. In some cases, status indicators may provide non-quantified status information about event occurrence, such as a simple non-numeric indicator that a series of events is reaching an end or that the user of the device should take some type of corresponding action; for example, flagging to a user that a substance being dispensed from a dispensing device in which the indicator apparatus is housed is reaching exhaustion. In some cases, status indicators may provide quantified status information about event occurrences, such as event counts. In such cases, status indicators are often referred to as event counters. When used within larger devices such as medicine dose dispensers, status indicators providing quantified status information about event occurrences can be referred to as "dose counters."

A common type of medicine dose dispenser is a metered dose inhaler, or "MDI." Integration of an event indicator apparatus, e.g. dose-counting mechanism, into inhalation apparatus-dispensing drug products, such as MDIs, enables users to assess how many doses remain in the obscured dispensing apparatus (e.g. canister of an MDI). Because of the critical nature of such information, it is now recommended that manufacturers integrate a dose-counting device into new MDIs as either a numerical countdown indicating the number of remaining doses or as color-coding indicating the device should not be used.

Several attempts have been made in the medical prior art to address this need and industry recommendation. U.S. Pat. No. 8,113,199, counterpart of International Patent Application WO2005/079727, and U.S. Pat. No. 9,089,661, counterpart of International Patent Application WO2007/124406, for example, disclose two such dose counter devices; however, these devices comprise a relatively high number of separate components adding risk of device failure, cost, and size. EP0269496 discloses a device with a push-button activation which may provide a simpler dose counter design in terms of the number of constituent parts; however, the use of a single counting wheel as disclosed in EP0269496 limits the probable usefulness of such a counter as the number of doses it is capable of counting is likely to be limited.

U.S. Pat. No. 5,988,496, counterpart of International Patent Application WO2005/060535, describes a dose counting mechanism comprising two counting wheels rotating about a common axis of rotation. The design of the device that is disclosed in the '496 patent is somewhat more efficient than, for example, the devices described in US813199 or U.S. Pat. No. 9,089,661; however, the design of the device disclosed in the '496 U.S. patent relies upon several components requiring a sub-optimal number of cooperating interactions to occur successfully for effective operation and the design of such devices may lead to undercounting due to when and how events are registered in such devices.

SUMMARY OF THE INVENTION

Provided herein are event-related status indicator apparatuses (sometimes called "indicator apparatuses") for stand-alone use or for incorporation into a larger device or system, such as a product (e.g., drug) dispensing device. The indicator apparatuses can be used with, or form part of, devices that measure events, such as dispensing devices, or other devices in which it is desirable to track the status of events, such as number of uses, amount of uses remaining, and the like.

In some embodiments, a dispensing device into which an indicator apparatus may be incorporated is a product dosing dispenser. According to some aspects, the dose dispenser may be a medicinal or pharmaceutical dose dispenser. Also or alternatively, the indicator apparatus of the present invention can be used in conjunction with any dispensing device having a mechanism present for applying an event trigger to the indicator apparatus to initiate the registration of an event. Also described herein are material and product dispensing devices, such as medical dose dispensing devices, incorporating an event-related status indicator apparatus having any suitable number of the various inventive features described herein.

The present invention relates in a particular aspect to an event-related status indicator apparatus comprising at least a first and second indicator structures, which typically are wheels, each indicator structure or indicator wheel comprising a set of event indicators which can operate together or independently to convey readable information concerning the status of events that the indicator apparatus is tasked with monitoring. While the indicator structure can be any suitable structure, wheels offer advantages in terms of size, workability, etc., and most of the disclosure provided herein refers to indicator wheels, although it will be understood that different shaped structures could be used in place of wheels and that even with respect to such wheels that the wheels can have various shapes, though typically the wheels will be circular or substantially circular.

An event-related status indicator apparatus of the invention will comprise event registration components or means for event registration, such as an actuator having a member capable of receiving an event trigger and a member capable of transferring the event trigger to a first wheel causing it to move upon the occurrence of each event, the first wheel event indicator changing to reflect the occurrence of the event upon each movement.

The inventive apparatuses also typically comprise first and second positioning elements and/or components, which together stabilize the second wheel and/or drive the movement of the second wheel. In one embodiment, these components comprise or consist of a first repositionable engagement unit and a second repositionable engagement unit, the first repositionable engagement unit engaging the second wheel to prevent its movement until it comes into contact with a first positioning element and the second repositionable engagement unit only engaging the second wheel to drive its movement when/after it engages a second positioning element.

In operation, upon a set number of events, the first positioning element repositions the first repositionable engagement unit to release the second wheel from a stabilized position, and substantially simultaneously, the second positioning element engages the second repositionable engagement unit to cause the second repositionable engagement unit to engage with the second wheel and cause its movement to a position such that the second wheel event indicator changes to reflect the occurrence of the event. Optionally, the event-related status indicator apparatus further comprises one or more status identifiers to identify which of the first set of indicators and which of the second set of indicators reflects the current event status (such identifiers optionally alternatively being part of an associated device and/or system or being both part of the apparatus and system). In operation, the first wheel rotates one increment upon each actuation while the second wheel rotates only upon every set number of events, unless otherwise prevented from doing so, such as for example if the event-related status indicator apparatus has reached a point of exhaustion.

BRIEF DESCRIPTION OF THE DRAWINGS/FIGURES

DETAILED DESCRIPTION OF THE INVENTION

Overview/Introduction

Figure 1:
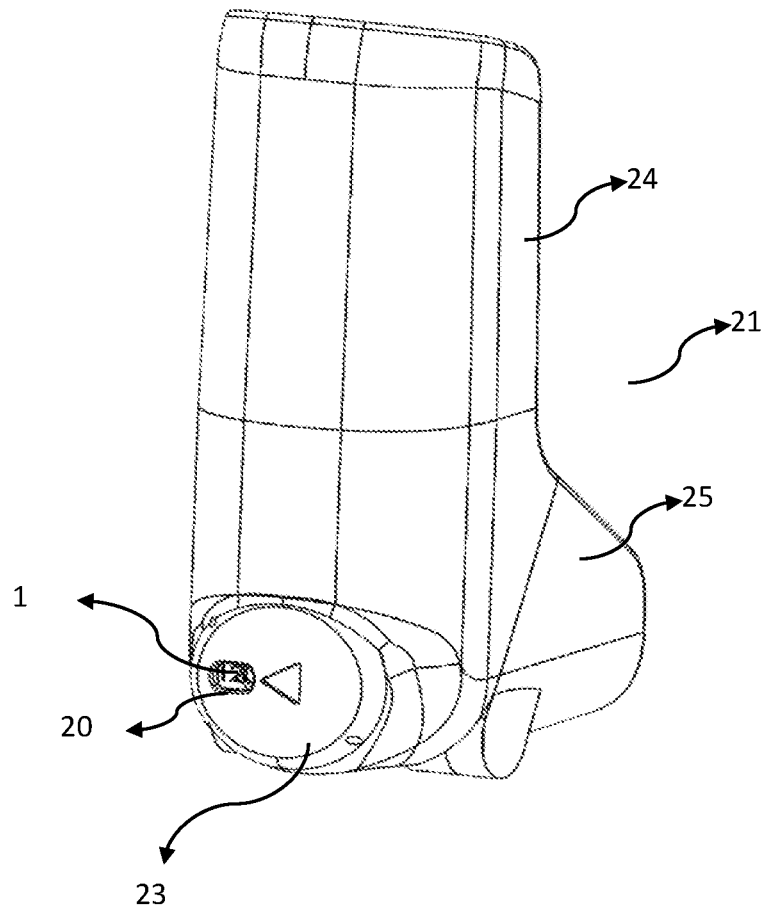
FIG. 1 shows an isometric view of an embodiment of the dispensing device.

Disclosed herein are new devices and components that are useful for indicating the event status of any type of event for which the event status may be desirable, such as when event status otherwise be unknown or difficult to determine. The apparatuses described herein can be classified as "components" in that they are often incorporated into or used as part of a larger device or system that incorporates other elements and functions, such as an MDI device. It will be understood herein that any of the terms apparatus, device, and component may be used interchangeably herein to refer to the inventive event status identifying machines described herein and that any description of, e.g., a device of the invention, should be interpreted as providing support for a component of the invention, and vice versa.

In a specific exemplary embodiment, the invention provides new devices for evaluating the status of dose administration of a medical dose dispensing product, e.g., indicating the number of doses dispensed or remaining available for dispensation.

The devices of the invention can be used as or in any suitable type of event measuring product, including any suitable type of media-dispensing or product-dispensing product, such as those which may be used in the food, chemical, agrochemical, or other technological fields and can measure any suitable aspect of an event, which may be the occurrence of an event and/or information about the event, such as the amount of material transported, deposited, or removed. Typically, an event in the context of the apparatus described herein means or comprises the occurrence of an event.

The inventive devices/components can be used in a number of different applications, examples of which are described in detail further herein. For example, devices provided by the invention can be used in a number of different applications, examples of which are described in detail further herein. For example, devices provided herein can find particular usefulness in the field of medicine and/or pharmaceuticals, in particular counting or indicating the number of doses dispensed from a medicine dispenser. Event indicator devices, e.g. dose counter devices also can find particular application in the field of propellant based pressurized inhalation aerosols delivered by oral and/or nasal administration systems; aqueous or non-aqueous systems for oral and/or nasal delivery; liquid dispensers for nasal delivery and powders for pulmonary administration and tablets, capsules, pellets or agglomerates for oral administration; or pre-filled syringes or pens or dispensers for intra-muscular or subcutaneous delivery. Accordingly, the event indicator devices, e.g. dose counters, and their related devices and methods of the present invention can be utilized as part of these and other medicament dispensing systems.

The devices provided herein typically will require relatively few components as compared to those systems previously known in the art (e.g., they may require 20 separate components or less, 15 components or less, 12 components, or even less than 10 components that are involved in the functioning of the counter). Devices of the invention also or alternatively are capable of registering event occurrences, magnitudes, and/or qualities, over a relatively large event measurement range (e.g. at least about 100 events in the case of a device that measures remaining events or occurred events). Devices of the invention also or alternatively can provide a relatively higher level of accuracy (e.g. a low false positive/false negative dose registration rate(s), mis-counts, or other/similar device failures) as compared to the prior art, particularly with respect to the functioning of the second indicator (wheel) of the system. Devices of the invention also or alternatively are capable existing in a relatively compact form/size (e.g., less than about 5 cm, less than about 4 cm, or even less than about 2.5 cm), and/or are relatively economical to produce as compared to previously described devices.

A detailed description of various embodiments of the invention is provided following a description of principles of construction designed to aid the reader in understanding this disclosure.

Principles of Construction

It is intended that the scope of the present disclosure should not be limited by any particular embodiment described herein. While various embodiments have been described above, it should be noted that they have been presented by way of example only, and not limitation. Numerous changes to the disclosed embodiments can be made in accordance with the disclosure herein without departing from the spirit or scope of the invention.

All headings and sub-headings are used herein for convenience only and should not be construed as limiting the invention in any way. The use of the terms "a" and "an" and "the" and similar referents in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range within an order of magnitude of the order of the range, including the endpoints (e.g., a range of 1-2 is to be interpreted as providing support for 1.0, 1.1, 1.2, 1.3, . . . 1.9, and 2.0; a range of 10-20 is to be interpreted as providing support for 10, 11, 12, 13, . . . 19, and 20), unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate—e.g., disclosure of "about 10" is to be understood as also providing support for 10 exactly). Terms of approximation, such as "about" are used herein where measurements are understood to vary due to measurement issues or variability in populations, such as results of clinical studies. The scope of such terms will depend on the context of the element at issue and the understanding of those skilled in the art. In the absence of such guidance in the art through relevant teachings or examples, "about" should be understood as meaning +/−10% of the indicated value(s).

As used herein, the singular form "a", "an", and "the" includes plural references unless clearly indicated otherwise and use of other singular forms include the plural and vice versa. Use of the term "or" herein is not meant to imply that alternatives are mutually exclusive unless clearly stated or clearly contradicted by context. In other words, "or" means "and/or" herein, unless expressly stated or otherwise clearly indicated.

All methods described herein can be performed in any suitable order unless otherwise indicated herein or otherwise clearly contradicted by context. Unless clearly indicated or contradicted by context the elements of a device disclosed herein can be manufactured in any suitable manner and by any suitable method. Unless otherwise stated or clearly contradicted by context, any combination of the various elements, steps, components, and/or features of the aspects described herein, and all possible variations thereof, are within the scope of the invention.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated. The breadth and scope of the present invention should not be limited by any of the above-described exemplary embodiments but should be defined only in accordance with the following claims and their equivalents.

The description herein of any aspect or embodiment of the invention using terms such as "comprising", "having," "including," or "containing" with reference to a component, element, composition, or set of compositions, components, or elements should be interpreted, whether explicitly stated or not, as simultaneously providing support for a similar aspect or embodiment of the invention that is "mostly composed of" (or "mostly comprises"), "consists of," or "consists essentially of," that particular element, elements, composition, or compositions, unless otherwise stated or clearly contradicted by context (e.g., a composition described herein as comprising a particular element should be understood as also describing a composition consisting of that element, or consisting essentially of that element, unless otherwise stated or clearly contradicted by context).

The term "substantially simultaneously" is used to describe two events that occur synchronously, that is, they take place together at about the same time, such as the two actions occur within about 5 seconds of one another, typically within about 2 seconds of each other, and usually about 1 second of one another or less, such as the two steps being completed within about 0.5 seconds, about 0.25 seconds, about 0.20 seconds, about 0.15 seconds, or about 0.1 seconds or less from one another, such as within about 0.05 seconds, about 0.025 seconds, about 0.01 seconds of one another or even less, such as within less than about 0.005 seconds or within about 0.001 seconds of one another or less, e.g., at the same time as one another (e.g., within the limits of detection).

Devices and Components Thereof

The event-status indicator devices/components of the present invention comprise a multi-component visual messaging system comprising two or more visual messaging components (e.g., indicator wheels), which are capable of and used to convey to a user information about current event status. Although the messaging components can operate on any suitable basis, typically one visual messaging component will operate upon every event to report and usually update the event status information and one or more second/secondary/other visual messaging components will operate every one or more set number of events (e.g., every $10^{th}$ event) to update the event status.

The event-status indicator device comprises a component which receives an event signal, energy, material, or other trigger (e.g. an "event trigger" or "trigger"), and which initiates the translation of the event trigger into an event registration. The detection of an event can be achieved by any suitable means. An actuator component, such as those exemplified further herein, or actuator mean component typically is incorporated into the device to detect the event and transmit energy, movement, or similar force to other parts of the device to impart movement of the moveable components responsible for changing the status of the status indicators. A registerable event can be any event wherein the actuator means or component is not locked and the actuator means or component receives sufficient energy from the trigger event to impart movement of the movable components responsible for changing the status of the status indicators. If the actuator means or component is locked, or the actuator means or component does not receive sufficient energy from the trigger event to impart movement of the movable components responsible for changing the status of the status indicators, the event can be a non-registerable event.

Typically devices of the invention comprise two or more multi-component repositionable engagement units and two or more positioning elements to modify the position of repositionable engagement units upon a certain number of events, wherein two or more repositionable engagement units operate substantially simultaneously upon every one or more set number of events to modify two or more visible messaging components to update the event status.

In embodiments, the actuation means initiating an event registration of the indicator apparatus is an actuator having an energy receiving member and an energy transfer member, the energy transfer member engaging with a first visual messaging component of the indicator apparatus. In common embodiments, the visual messaging components of the visual messaging system can be a first wheel and a second wheel, each comprising readable event indicators capable of conveying information to the user related to the current event status, the first wheel participating in providing the updated event status upon every event and the second wheel participating in providing the updated event status upon every set number of events.

In common embodiments, the multi-component engagement system also comprises two repositionable engagement units. In some aspects, the first repositionable engagement unit is designed as a stabilizing component capable of being positioned in a first, stabilizing, position or a second, non-stabilizing, position, preventing the second wheel from participating in an event registration when in the stabilizing position. In some aspects, the second repositionable engagement unit is designed as a driving component capable of being in a first, non-engaged, position and a second, engaged, position, driving the second wheel to participate in an event registration when in the engaged position. In some aspects, the repositionable engagement units are each modified from their first to their second positions by two independent positioning elements, each positioning element interacting with one repositionable engagement unit to move it from its first position to its second position. In common embodiments, the repositioning of the repositionable engagement units occurs substantially simultaneously every set number of events, e.g. every tenth event, registered by the event-status indicator apparatus so as to substantially simultaneously free the second wheel for rotation and drive the second wheel to rotate to participate in the event registration. In some aspects, the engagement of the two repositionable engagement units with the second wheel is performed via a latching mechanism present on the second wheel, in some cases this mechanism is set of "teeth."

In common embodiments, an actuator, comprising one member to receive energy of an event trigger and a second member to transfer the energy of an event trigger initiates the registration of an event upon every event trigger. In some aspects, the element of the actuator transferring the energy from the event trigger is an actuator pawl, the pawl engaging with a latching mechanism on the first wheel, the first wheel being the recipient of the actuation energy from the actuator. In one embodiment the first wheel latching mechanism is a set of teeth.

In one embodiment, the event-status indicator apparatus further comprises a base to maintain the first and second wheels in position relative to one another. In some embodiments, one or more of the repositionable engagement units and/or positioning elements is attached to or is an integral part of the first wheel and one or more of the repositionable engagement units or positioning elements is attached to or is an integral part of the base.

In some embodiments, the indicator apparatus is associated with (e.g., contained in) a larger device that causes, processes, modifies, measures, or otherwise is associated with the measurable event(s). The indicator apparatus can be, e.g., housed within a medicament dispenser, for example within the dispenser body of the medicament dispenser, which may further comprise components for storing and administering medicine to a subject or patient (e.g., a mouthpiece).

In some aspects, the body of the apparatus or associated device (e.g., a medicament dispenser) can comprise a status identifier that identifies which of the event indicators on the first and second wheels reflects the current event status. In one exemplary embodiment, the device is a medicament dispenser, such as a metered dose inhaler containing an dispenser body for holding a medicament container, a medicament access body in the form of a mouthpiece, a protective cover of the medicament access body in the form of a hinged cap, and event-related status indicator apparatus comprising the elements and their common or alternative aspects and/or embodiments as described herein, and a status identifier window in the body of the medicament dispenser for viewing the event status as displayed by the event-related status indicator housed within.

According to certain embodiments, a successful event trigger is an event trigger comprising a sufficient amount of energy so as to force the rotation of the first wheel of the indicator apparatus one increment; exemplary mechanisms for advancement are described in detail herein.

An event trigger can be any event capable of activating the actuator/actuation means. The event trigger can also or alternatively be referred to as an activation trigger, actuation trigger, actuation trigger event, activation event, actuation event, or simply an actuation. The event trigger can be a mechanical trigger, such as for example a trigger caused by, inter alia, pressing, depressing, compressing, squeezing, twisting, turning, pulling, pushing, pulsing, rotating either an element of the actuator itself or a component in contact with the actuator. Also or alternatively, the event trigger can be the release of an associated composition, such as the dispensation of a chemical or medicament housed within a dispensing device along with the indicator apparatus. In some aspects the event trigger could be a pneumatic pressure, such as a blowing force or a sucking force, or similar or equivalent change in air velocity or air pressure. In some embodiments, an event trigger can be an energy in the form of an electrical signal, change in temperature, light signal, sound signal, vibrational movement, combination thereof, or any application of energy receivable by the actuator. Numerous suitable examples of such actuators are known in the art, and, accordingly, need not be described herein in detail.

According to certain embodiments, the actuation trigger is the movement of a medicament container, e.g. a "squeeze" applied by the user to a device, such as an MDI, such that a material storage component (e.g., a medicament canister) is pushed downward, and the event trigger is received by the actuator as a mechanical energy of movement. According to alternative embodiments, other types of mechanical means operate as event triggers, such as the pressing of a button, tab or equivalent of a dispensing device. In one example such a pressing of a button, tab, or equivalent can be received by the actuator as a mechanical force and transferred to a mechanism which activates a needle mechanism for dispensing an injection. In some aspects an event trigger, the energy received from the event trigger, the transfer of energy from the event trigger, or any combination of the event trigger, energy receipt, or energy transfer, can be quick and forceful, such as may occur if the indicator apparatus is used in auto-injection device. In other aspects, the trigger can be a rotational trigger, such as the twisting or turning of an element in order to dispense a medicament. According to another aspect, the trigger can be an inhalation, or a sucking (negative) pressure, by a user of medicament held within the medicine dispenser in which the actuation means resides such as in an embodiment wherein the indicator apparatus is housed within a metered dose inhaler. In one aspect, the event trigger can be a direct trigger, such as a user directly pressing on the actuator. According to one embodiment, the event trigger is a mechanical pressure applied to an element of the actuation means forcing movement of the actuation means in a linear direction.

In some embodiments the actuation means can be any actuation means capable of receiving an effective amount of energy from an event trigger and transferring an effective amount of energy from the event trigger to a component of the indicator apparatus so as to register an event. According to certain embodiments, the actuation of an event count is initiated by the movement of the first wheel of the indicator apparatus. In certain aspects the indicator apparatus comprises an actuation means capable of receiving an effective amount of energy from an event trigger and transferring an effective amount of energy from the event trigger to the first wheel so as to move the first wheel to an extent sufficient to register an event.

In one aspect, the actuation means can be a mechanical means comprising one member which receives the energy from an event trigger and a second member which transfers the energy from an event trigger to a receiving element. In one aspect, the actuation means can be an electronic circuit, a light sensor, a temperature sensor, a sound sensor, a movement sensor, or any similar or equivalent sensor, component, mechanism, or system capable of receiving an energy from a first source and transferring that energy to a target. In some embodiments, the actuation means of the indicator apparatus is a mechanical means for receiving the energy from an event trigger and transferring the energy received from the event trigger to the first wheel so as to force its movement and initiate a dose registration. In some aspects, the actuation means is an actuator device/component, such as those exemplified and/or described further herein.

An actuator component ("actuator") can be a movable, mechanical element comprising a member capable of receiving the energy arising from one or more relevant event or actuation triggers, also referred to herein as the "energy receiving member", and a member to transfer that energy to a second component of the indicator apparatus, also referred to herein as the "energy transfer member". In common embodiments, the energy transfer element transfers the energy from the event trigger to the first wheel. The actuator can comprise or consist of any suitable component, set of components, device, or system for performing these functions. According to one embodiment, the actuator is a plunger comprising an energy receiving element and an energy transfer element.

According to certain embodiments, the actuator is a part of the indicator apparatus device. According to alternative embodiments, the actuator is a part of the overall system which makes up the indicator apparatus. In some embodiments, the actuator is designed as an element of a dispensing device in which the remaining components of the indicator apparatus are housed.

According to one embodiment, the energy receiving member receives or maintains a physical contact with a component of an associated device, such as a dispensing device. In some aspects, the event trigger is the actuation of that associated device. For example, in an embodiment where the indicator apparatus is housed within a MDI, the event trigger can be the squeezing of the medicament canister or dispenser housing wherein it resides as the user attempts to actuate the device to dispense a medicament housed therein, upon which an element of the medicament canister or dispensing device housing presses down on the energy receiving member of the actuator.

The energy receiving member of the actuator can, in some embodiments, not be in contact with an element of a dispensing device prior to an event trigger. In alternative embodiments, the energy receiving member of the actuator may be in contact with an element of a dispensing device prior to an event trigger, simply not receiving an actuation energy from the element until an event trigger occurs. Once an event trigger occurs, the energy receiving member can maintain contact with the component of the dispensing device throughout part of or the entirety of the event trigger and resulting actuation motion. Such contact can facilitate the transmission of the energy of an event trigger to the second component of the indicator apparatus, e.g. the first wheel.

The energy receiving member of the actuator can be a linear rack, shaft, plate, platform, tab, boss, pin, plunger, rod, or other similar or equivalent means of receiving energy arising from a relevant event trigger. According to certain embodiments, the energy receiving member of the actuator is immobile relative to one or more other members of the actuator. According to alternative embodiments, the energy receiving element can move relative to one or more other members of the actuator.

According to common embodiments, the energy receiving member of the actuator is a plunger, boss, or pin, or an equivalent/similar structure used by those of skill in the art. In some aspects, the boss may be designed to fit within a correspondingly shaped hole in a dispenser body. In some aspects, the energy receiving member is a circular boss or circular pin. In some aspects, the boss or pin directly receives the force applied to actuator from the event trigger. The receipt of this trigger can begin the set of activities required to register an event on the indicator apparatus.

The receipt of energy from an event trigger by the energy receiving member can move the actuator in any suitable direction, such as in a substantially or essentially entirely linear direction. According to some embodiments, the linear axis upon which the actuator travels, which may also be referred to as the axis of actuation, is in line with or intersects the linear axis upon which the first and second wheels rotate. According to alternative embodiments, the linear axis upon which the actuator moves does not intersect the longitudinal axis upon which the first and second wheels rotate. In one embodiment, the linear axis upon which the actuator moves is offset to the longitudinal axis upon which the first and second wheels rotate. That is, upon actuation, in response to the receipt of energy from an event trigger by the boss or pin, the actuator moves in a linear direction along an axis offset to the longitudinal axis upon which the first and second wheels rotate. In some aspects, the device comprises an axis of actuation offset from the longitudinal axis of rotation of the first and second wheels which results in a detectable torque, which according to certain aspects detectably aids in the registration of an event by movement of one or more event-registering components of the system, and, according to more particular aspects, is a sufficient amount of torque to be applied to the element of the indicator apparatus receiving the actuation energy from the actuator, e.g. the first wheel, for it to register an actuation under appropriate conditions.

In one aspect the actuator comprises one or more members capable of transferring the energy received from an event trigger to a second element of the indicator apparatus. An energy transfer member can have any size, shape or design capable of cooperating, communicating, or otherwise interacting with or engaging a second component of the indicator apparatus. In one embodiment, the first wheel of the indicator apparatus is the recipient or target of the energy transfer.

An energy transfer member/component can be mechanical means of engaging with a second component of the indicator apparatus. For example, the energy transfer member can be an arm, tab, ridge, clip, catch, notch, pawl or similar elements or any combination of such elements which function to transfer energy arising from a relevant event trigger of the second component of the indicator apparatus via the actuator. In some aspects, the energy from an event trigger can be transferred to the second component via a mechanical engagement.

The energy transfer member can be designed to have a shape complementary to the component of the indicator apparatus to which it transfers energy. In one embodiment, the actuator energy transfer member is a pawl. The actuator pawl can be a latch-like device designed to engage with the first wheel of the indicator apparatus.

The energy transfer member, e.g. actuator pawl, can be attached to the actuator at one end and free at the opposite end, such as e.g. in an arm design. Such a configuration creates a movable, flexible, in some aspects spring-like design, allowing the actuator pawl to bend or flex slightly in response to pressure. The free end of the actuator pawl can be free to engage with other indicator apparatus components, such as the first wheel to transfer an actuation force.

An energy transfer member, e.g., an actuator pawl, can comprise a "catch" element at its free end which can further facilitate the engagement with or directly engage with the indicator apparatus component receiving the energy transfer. The catch on the free end can have a specific shape or comprise an element such as a knob, bump, notch, protrusion, latch, tooth, or similar or equivalent shape which cooperates, interacts, or engages with another device component. In some aspects, the device component with which it interacts can have a complementary shape. According to one embodiment, the actuator of the indicator apparatus of the present invention comprises an actuator pawl which further comprises a catch in the form of one or more fixed teeth, a distinct shape at its end which protrudes outward from the end of the actuator pawl resembling a latch "tooth" (e.g. having a square-, rectangular-, triangular-, trapezoidal-, or polygonal-shape which aids the actuator pawl in the engagement of the actuator component with a second component).

In one embodiment, the actuator comprises a pawl with a catch in the form of a fixed tooth which engages with the indicator apparatus first wheel. The actuator pawl fixed tooth can be in the form of a ratchet tooth which can engage with a complementary ratchet tooth latching mechanism of the first wheel, described elsewhere herein. The actuator pawl, having a catch, e.g. a fixed ratchet tooth, provides the mechanism for the actuator's engagement with the first wheel to facilitate the event trigger energy transfer. The first wheel can be designed to cooperate, communicate, interact, or otherwise engage with the actuator, e.g. the fixed ratchet tooth of the actuator pawl, for example having one or more complementary receiving areas for the fixed ratchet tooth of the actuator pawl which again is described elsewhere herein.

The energy transfer member can be an integral element of the actuator, the energy transfer member being manufactured as part of the actuator (e.g. as a single element). Alternatively, the energy transfer member can be manufactured as a separate component from the actuator and later fastened to the actuator by way of glue, a tongue-and-groove fastening mechanism, screws, clips, snap fit, heat staking or heat welding or other means of attachment to the actuator pawl. Further, the catch mechanism can be an integral element of the energy transfer member, the catch mechanism being manufactured as part of the energy transfer member (e.g. as a single element). Alternatively, the catch mechanism can be manufactured as a separate component from the energy transfer member, being later fastened to the energy transfer member by way of glue, a tongue-and-groove fastening mechanism, screws, clips, snap fit, heat staking or heat welding, or other means of attachment to the energy transfer member.

According to one embodiment, the actuator receives energy from an event trigger from one direction and transfers it in a second direction. In some embodiments, the first (trigger-applied) and second (transferred) directions can be the same, e.g. the same linear direction. In some embodiments, the first and second directions can be different directions. Also or alternatively, the actuator can be designed such that it is capable of transferring the actuation energy in a second direction that is substantially or actually perpendicular to the direction from which the actuation energy was received. In other embodiments, the actuator transfers the energy in the same or substantially the same direction as it is received. The transfer of the energy can in either case cause an indicator, such a wheel, to move in any suitable direction with respect to the direction of transfer.

For example, according to certain embodiments, the indicator apparatus includes the operation of the actuator means, e.g. an actuator as described previously, receiving energy from an event trigger in the form of a motion and transferring that motion to a second element of the indicator apparatus. In some aspects, the motion of the actuation or event trigger is a substantially, essentially, or entirely rectilinear motion. In other aspects, the motion of the actuation or event trigger is a rotational motion, such as the type of motion used to open a bottle or turn a knob or valve so as to provide a release or disengagement of elements or dispensation of a substance or composition held within.

In some embodiments, rectilinear motion of an actuator or event trigger is converted to a rectilinear motion of the actuator. In some embodiments, the rectilinear motion of the event trigger is converted to a rotational motion of the actuator. In one embodiment, the rectilinear motion of the event trigger is received as energy of motion and causes a rectilinear motion of the actuator which is then transferred to a second component of the indicator apparatus to cause a rotational motion of the second (receiving) component of the indicator apparatus. In further embodiments, an event trigger in the form of rotational motion, e.g. a twisting or turning such the operation of a screw mechanism of, e.g. a dispensing device in which the indicator apparatus is housed is mechanically converted to rectilinear motion of the actuator which is further transferred to the transferred energy receiving component causing rectilinear motion or rotational motion of the receiving component. Irrespective of the direction from which energy is received by the actuator energy receiving member or to which the energy is transferred by the actuator energy transfer member, the receipt and transfer of the energy from a trigger event typically instigates movement of the indicator and, accordingly, a change in event indication status.

Event-related status indicators are designed to register the occurrence of multiple events. Therefore, the design of an event-related status indicator can benefit from the incorporation of a means to re-set the actuation means such that it may be re-set upon conclusion of an event and re-actuated upon the next event. In a circumstance wherein the actuation means does not become re-set and available for re-actuation, the indicator apparatus could not be re-actuated and therefore could not register subsequent events if/as they occurred. This may be a beneficial design option for the end of an event registration cycle, such as, for example, in an embodiment wherein the indicator apparatus is housed with an medicament dispenser, the dispensation of a dose of medicament being the events registered, when insufficient medicament remains in a medicament container to administer a full dose. In such a case, an inability to actuate the medicament dispenser due to the actuation means not being in a position for re-actuation can be or contribute to a signal to the user that the medicament has been exhausted.

According to certain embodiments, the actuation means or actuator includes or is accompanied by one or more mechanisms to assist, direct, guide, be completely responsible for or is otherwise capable of returning the actuator means to a start position after an actuation has occurred. According to certain embodiments, the mechanism for returning the actuator back to a starting position can be any means capable of returning the actuation means to a starting position. For example, the return means could be a flex arm, flex tab, flexible and/or compressible material element such as sponge, foam, rubber or other material capable of being depressed and returning to a start position after depression or compression, an inflatable element again capable of being depressed and returning to a start position after depression or compression, or such a similar or equivalent element.

In one embodiment, the mechanism for returning the actuator back to a starting position is a spring. In some aspects, the actuator has an arrangement to attach a spring to assist the return movement of the actuator after actuation/activation or operation. The spring can be attached to actuator. The spring can also or alternatively be attached to a dispenser body. Also or alternatively, the spring can be attached to both a dispenser body and the actuator. One or more elements which return the actuator to a start position after each actuation can be manufactured as part of a dispenser body, part of the actuator, part of both the dispenser body and the actuator, or as an independent element. The one or more elements can be manufactured from the same one or more materials as any one or more of the materials of which the indicator apparatus or dispenser components are manufactured. Also and alternatively, the one or more elements can be manufactured of one or more materials different from the one or more materials used to manufacture the indicator apparatus or dispenser. For example, the indicator apparatus and/or dispenser in which it may be housed can be manufactured from one or more hard polymers and the element assisting, directing, guiding, being completely responsible for, or otherwise capable of returning the actuator to a start position after an actuation has occurred can be made of a metal, e.g. as in a metal spring.

The means for returning the actuator to a starting position can act upon a manual trigger or automatically at the end of an actuation event. For example, actuation of the actuator could be similar to the ejection of a pen tip in a retractable pen wherein the "event trigger" is the depression of the plunger on a pen which forces the tip of the pen out from the pen housing so as to enable its use. A manual means of resetting the indicator apparatus can be a reset switch or button such as, for example, those which can be pressed on the body of a retractable pen so as to retract the tip and return it to the inside of the pen housing when the user is finished with the pen. Alternatively, the means for returning the actuator to a starting position can be an automatic mechanism, such that upon the completion of an actuation, unless otherwise restricted from doing so, the actuator utilizes a stored energy, e.g. a compression energy created by the depression of a spring during an actuation stroke, to automatically return the actuator to its starting position.

According to certain embodiments, the means for assisting, directing guiding, being completely responsible for, or otherwise capable of returning the actuation means to a start position after an actuation has occurred can operate cooperatively with the indicator apparatus such that in circumstances wherein the indicator can become locked (e.g. when housed within a medicament dispenser and the medicament container has no remaining full doses of medicament and also or alternatively when the indicator apparatus has reached its lowest or highest count, also described as the indicator apparatus having reached the end of its life cycle), the means for returning the actuation means to its starting position may be inhibited, such that the actuation means remains in a depressed or otherwise activated position, does not return to a start position, and therefore cannot be re-activated. In such a manner, a dispensing device in which an indicator apparatus may be housed can be adapted to prevent the dispensing device from being actuated after a predetermined number of events, e.g. dispensations, have been registered. According to certain embodiments, this may be the case when the medicament dispenser is fully exhausted (e.g. empty or otherwise inoperable).

According to one embodiment, an energy transfer element, e.g., an actuator pawl, is capable of "riding over," or passing over, or otherwise not engaging (or at least not movingly engaging) with the latching mechanism (e.g., teeth) of the energy receiving component, e.g. the first wheel in at least certain events/times during actuations. According to one embodiment, as the actuator is returned to its original position by the incorporated return mechanism, the actuator pawl fixed ratchet tooth can slide over the element with which it engaged on the actuation of the actuation means (e.g. the first wheel latching mechanism), such that it returns to a start position while not further engaging with the first wheel latching mechanism so as to cause further rotation of the first wheel while doing so. The actuator can then complete the actuation stroke, placing the first and or first and second wheels in position of having completed a single increment of rotation, the details of which are discussed elsewhere herein. Hence the fixed ratchet tooth (exemplary of catch element on an energy transfer member of the actuator intended to engage with a second component, e.g. the teeth on the first wheel of the indicator apparatus) can be shaped such that a first side has a shape complementary to a first side of the element with which it is intended to engage (e.g. a complementary clip or latch shape), while the second or opposing side can have a shape which facilitates the sliding of the one component over the other (e.g. the fixed tooth of the actuator pawl over the ratchet tooth of the first wheel) as is commonly understood as a ratchet mechanism. Such a shape may be, for example, an angled or rounded edge or side. Additionally, the component with which it engages, for example the ratchet tooth or teeth of the first wheel, can have a shape on a first side that is complementary to the first side of the, e.g. fixed ratchet tooth and a shape on the opposite side which further facilitates the sliding of the one component over the other (e.g. the actuator pawl fixed tooth over the first wheel ratchet tooth). According to such a design, when in motion (caused by an actuation trigger) in a first actuation/activation direction (e.g. downward), the complementarily-shaped side of the fixed ratchet tooth on the actuator pawl being engaged with the second element of the indicator apparatus (e.g. first wheel ratchet tooth) imparts an energy to that element and forces it to move, for example forcing the first wheel to rotate. When the actuation trigger is complete and the actuation means is in motion to its return position (e.g. a direction opposite that of its initial activation direction, for example upward), the actuator pawl fixed ratchet tooth disengages with the previously-engaged ratchet tooth of the first wheel, the fixed tooth rides over an adjacent ratchet tooth while the first wheel remains stationary, and reengages with the next ratchet tooth once the actuation means has returned to its original or starting position such that it is in position to rotate the first wheel upon the next actuation initiated by an event trigger and the first wheel or first and second wheel as will be described elsewhere herein, have completed a single increment of rotation.

In some aspects, the device comprises an actuation energy transfer component and a first wheel latching mechanism which together are configured and/or operate as a ratchet mechanism, which both facilitates registration of an event and also inhibits or prevents rotation of the inner wheel in an opposite direction from the direction associated with registering additional events. For example, an actuator pawl fixed ratchet tooth and a ratchet-tooth latching mechanism on the first wheel are configured so as to detectably inhibit or prevent (under normal operating conditions) reverse rotation of the inner wheel. According to certain embodiments, as the actuator pawl fixed ratchet tooth disengages from the ratchet tooth of the latching mechanism on the first wheel after receipt of an actuation energy, the actuator pawl fixed tooth can "slide" or "ride" over an adjacent ratchet tooth of the first wheel latching mechanism (or otherwise move over or along without engaging in a manner that causes a movement associated with event registration or reverse rotation of the first wheel). Such "sliding", or "riding", of the actuator pawl fixed ratchet tooth over a first wheel ratchet tooth can allow for the actuator to return to a start position (or next position) such that it is capable of receiving and reacting to a new actuation or subsequent actuation energy while not sufficiently engaging with the first wheel so as to cause it to rotate in a reverse direction. The shape of the actuator pawl fixed ratchet tooth, and the shape of the ratchet tooth of the latching mechanism on the first wheel can be such that while the actuator is traveling in a direction toward its starting position, there is no component of the actuator pawl fixed ratchet tooth shape which can engage (or at least movingly engage) with the ratchet tooth on the first wheel over which it slides or rides to an extent sufficient to force the first wheel to rotate. According to some embodiments, the reverse rotation of the first wheel is prevented by use of a ratchet mechanism. According to some embodiments, the reverse rotation of the first wheel is prevented by use of a ratchet mechanism alone. According to alternative embodiments, the reverse rotation of the first wheel is prevented by use of a ratchet mechanism in conjunction with one or more secondary means of preventing undesirable rotation of the first wheel, such as for example but not limited to the engagement of the second wheel catch mechanism on the flex drive arm of the first wheel and the latching mechanism of the second wheel as is described elsewhere herein.

According to certain embodiments, in its resting, starting, next, or original position, e.g. prior to an actuation or upon the completion of an actuation, the actuator pawl fixed tooth and the space between ratchet teeth of the first wheel latching mechanism, can comprise shapes such that the actuator pawl fixed tooth "nests", or fits complementarily within the space between the ratchet teeth of the first wheel latching mechanism. Such a complementary fit between such components can, e.g., provide a means of preventing or a least detectably inhibiting the first wheel from rotating in either direction while in a resting position, both sides of the actuator pawl fixed tooth making sufficient contact with, or capable of making sufficient contact with, sides of first wheel latching mechanism ratchet teeth above and below the actuator pawl fixed tooth so as to block the first wheel from inadvertent rotation in either direction.

The first wheel can comprise design elements that allow it to cooperate, communicate, interact or otherwise engage with other components of the indicator apparatus. Such elements can comprise a latching mechanism (e.g. a first set of teeth), a means, mechanism or element for engaging with the second wheel, and an element capable of causing a modification of position of a base element. Each design element of the first wheel can further comprise varying additional elements aiding in its functionality which will be described further herein.

The first wheel can have generally a disc, ring, or circular shape. According to certain aspects, a first face of the first wheel can comprise elements which all lie on or substantially on the same plane, having no raised or depressed areas that vary significantly from a single plane (or that vary from the surface by less than about 15%, less than about 10%, or less than about 5% of the thickness of the surface). According to alternative aspects, a first face of the wheel may comprise elements such as a raised inner or outer edge, lower inner or outer edge, or raised, embossed, carved or etched communication elements such as event indicators as to the status of doses available in the medicament dispenser. Such communication elements will be described further elsewhere herein.

According to aspects a second side of the first wheel can comprise elements which protrude from the second side so that the elements do not all lie substantially within the same plane.

For sake of orientation, as used herein the "front" side or face of the first wheel is the side or face comprising event indicators (visual communication elements), to be described elsewhere. The "back" side or face of the first wheel is the side or face comprising the latching mechanism and does not comprise event indicators.

According to embodiments, the element of the first wheel capable of and designed for receiving the actuation energy from the actuator means is a latching mechanism. The first wheel latching mechanism can be any mechanism capable of engaging with another element of the indicator apparatus, such as for example the energy transfer member of the actuator, or even more specifically, such as a catch on the energy transfer member of the actuator, Such a mechanism can be, for example, one or more insets or one or more protrusions shaped to receive, interact, cooperate or engage an element with a complementary shape. In one aspect, the first wheel latch mechanism is a first set of teeth. In one aspect this set of first wheel teeth can comprise a number of ratchet teeth.

As used herein, the term "ratchet tooth" or "ratchet teeth" is a tooth or set of teeth shaped such that they cooperatively engage with and receive a first force or motion causing a rotation of the element on which they reside in one direction, however their shape allows them to resist or avoid rotation in an opposite direction upon a second force or return motion. Ratchet teeth can be of any suitable size or shape, such as rectangular, square, triangular or pyramid shaped, semi-circular, oblong, or squircular shape, or have any type of trapezoidal, polygonal, or any shape which can interact with another element of the mechanism having a complementary shape or any shape capable of interacting with a tooth having such a structure, yet capable of resisting, deflecting, or avoiding receiving or reacting to a force or motion upon a return motion of an interacting element. Such ratchet teeth can have a complementary shape to a fixed ratchet tooth of an actuator pawl.

According to one embodiment, the actuator pawl rides over, or passes over, or otherwise does not engage with the latching mechanism of the first wheel (e.g. first wheel first set of teeth) when the dispensing device is returning to the original or non-dispensing position. Further, as will be described elsewhere herein, the engagement of the second wheel catch mechanism on the flex drive arm of the first wheel and the latching mechanism of the second wheel prevent reverse rotation of the first wheel when the driver is returning to its original or non-dispensing position. According to some aspects, once the actuator pawl has returned to its original position after an actuation, or also or alternatively when the actuator pawl is in its original or starting position prior to an actuation, the latching mechanism design of the actuator pawl fixed tooth and the ratchet tooth design of the latching mechanism of the inner wheel provide additional means of preventing rotation of the first wheel, as the complementary design of the elements of the latching mechanism mechanically prevents or at least detectably inhibits undesirable first wheel rotation (e.g., rotation in a direction that is opposite the direction associated with registering the next event).

According to one embodiment, the engagement of the actuator pawl fixed ratchet tooth with the first wheel latching mechanism, e.g. ratchet teeth, transfers the event trigger actuation energy from the actuation means (e.g. actuator) to the first wheel, driving the first set of teeth on the first wheel and causing the first wheel to rotate. The first wheel first set of teeth can have any number of teeth, such as 1 to greater than 100 teeth, more commonly 5 to 50 teeth, even more commonly 10-20 teeth. In one embodiment, first set of teeth on the first wheel has 10 teeth.

The first wheel latching mechanism is positioned so as to be accessible to, and can be in contact with, the energy transfer member of the actuator. More specifically in a demonstrative embodiment, the teeth of the first wheel are positioned so as to be accessible to, and in contact with, the actuator pawl, even more specifically being in contact with the actuator pawl catch mechanism (e.g. fixed ratchet tooth). The first wheel can comprise ratchet teeth arranged on its surface.

More specifically, according to certain embodiments, the teeth of the first wheel are ratchet teeth which are arranged on a boss. As used herein, a "boss" is a protruding feature. As an element of the actuator, a boss is an element that protrudes outward from the actuator and, according to certain embodiments, can function as an energy receiving member to receive energy from an event trigger. As an element of the first wheel, a boss is an element which can protrude from the back of the first wheel. The first wheel boss can be circular, polygonal, tubular, or cylindrical in shape and can be centrally located within the first wheel. The first wheel boss can have an opening therethrough which defines the center of both the boss and the first wheel as a whole.

The diameter of a boss can be smaller than the outer diameter of the first wheel. According to some embodiments, the diameter of the boss is at least 10% smaller than that of the outer diameter of the first wheel, such as for example at least 10% smaller, at least 15% smaller, at least 20% smaller, at least 25% smaller, at least 30% smaller, at least 35% smaller, at least 40% smaller, at least 45% smaller or even greater, such as approximately 50% smaller, at least 55% smaller, at least 60% smaller, at least 65% smaller, or at least 70% or 75% smaller or even more. According to some embodiments as will be further described herein, the first set of teeth of the first wheel may be incorporated into or onto this central boss. The boss can be centrally located on the wheel (i.e., can be a central boss). Accordingly, as in some embodiments the first wheel first set of teeth receive the actuation force from the actuator and hence cause the first wheel to rotate, the diameter of the central boss, and the size of the first wheel teeth therein or thereon may dictate the rotational distance covered by a single increment of rotation of the first wheel.

A boss can aid in securing the first wheel within the base, an element of the indicator apparatus to be described elsewhere herein. The base, as described elsewhere, can have a hole, e.g., a hole in its center. Such a hole can be designed in shape such that it can receive a boss of the first wheel, such that the first wheel can nest or sit within the base. Such a configuration can aid the various elements of both the first wheel and base, to align, communicate, cooperate, interact, or engage with one another as is required for successful operation of the indicator apparatus.

According to some embodiments, the first wheel comprises a circular boss, protruding from the back of the first wheel, such boss designed to fit smoothly yet securely within a cooperatively sized and shaped hole within the base, so as to provide means for the first wheel to sit or nest within the base, while being free to rotate within the base unless otherwise impeded, the boss further comprising the first wheel latching mechanism toward its far end which extends through the hole in the base such that the latching mechanism is accessible to the energy transfer member of the actuator. The first wheel first set of teeth can protrude from the end of the central boss so as to define the end of the central boss or alternatively can be arranged so as to extend above and around the circular boss. According to a different design the teeth can be carved into, or out of, the central boss so as not to add additional height or thickness to the central boss yet provide for the teeth to be in the outer, circumferential surface of the boss. According to certain embodiments, the first wheel comprises a circular boss protruding from the back side of the first wheel, the circular boss further comprising a first set of teeth having a ratchet design, the ratchet teeth positioned at the end of the circular boss, and further the ratchet teeth having a polygonal shape of complementary shape to that of a fixed ratchet tooth on the actuator pawl, such that the actuator pawl ratchet tooth can fit securely within any one ratchet tooth of the first wheel.

A boss can be constructed within the first wheel such that the first wheel comprising the boss is a single unit. Alternatively, a boss can be manufactured as a separate unit and attached (e.g. by screws, glue, clips, tongue-and-groove, snap fit, heat staking or heat welding, or other similar or equivalent fastening mechanisms) to the back side of the first wheel.

In some aspects, the first wheel is capable of rotation, e.g. in a clockwise or counterclockwise direction. In some aspects, when free of any impediment, the first wheel is capable of rotation in both a clockwise and a counterclockwise direction. The first wheel can encounter impediments, such as interaction with other components of the indicator apparatus, which can impede its rotation in a certain direction, forcing a capability to only rotate in a single direction under certain circumstances as will be further detailed herein. In some aspects, the first wheel can further be provided with a central bore or hole. According to certain embodiments, the central bore or hole can act as a bearing for the central axis of the indicator apparatus, about which the one or more wheels of the indicator apparatus can rotate. In some aspects, the central bore or hole can facilitate mounting or securing the indicator apparatus within or to a larger device, e.g. a medicine dispenser. For example, the larger device body can have a pin, shaft, boss, or other similar or equivalent structure capable of fitting within the central bore or hole of the first wheel in such a manner that the inner wheel can slide over the structure, structure then serving to hold the inner wheel in position relative to the larger device, maintaining its position without impeding the rotation of the inner wheel when the inner wheel is called upon to rotate under certain conditions. In some embodiments, such a mounting support can be the sole mounting mechanism. In some embodiment, such a mounting support can be in addition to other mounting supports, such as those provided by mounting elements present on a base component of the indicator apparatus.

The event-related status indicator apparatus of the present invention can further comprise a means for intermittently or after a set number of events, engaging the second wheel to drive its rotation in conjunction with the first wheel. Such a driving means can be any means, e.g. any unit, element, or component capable of being in a position to interact with, contact, or otherwise engage with, or be disengaged from, the second wheel and is movable from one position to another. For example, the means can be a repositionable arm, a selective switch, a movable hook, catch, latch, or other similar or equivalent mechanism for engaging or disengaging the second wheel according to certain conditions and when engaged, drive its rotation.

In some aspects, the event-related status indicator apparatus can comprise two repositionable engagement units, each engaging the second indicator wheel, however each engaging the second indicator wheel to perform a different function. Repositionable engagement units can be elongated members. The repositionable engagement units can be fixed, e.g. immobile, on one end and movable on a second end. According to one embodiment, the means for engaging the second indicator wheel so as to drive its rotation is one of the repositionable engagement units of the indicator apparatus.

In embodiments the repositionable engagement unit which engages the second wheel under certain conditions is a repositionable or flexible arm attached to the first wheel. According to embodiments, the flexible arm responsible for driving the second wheel is the only arm on the first wheel; that is, the first wheel does not contain or is not bound to more than one flexible drive arm. Such an element may be referred to as a repositionable engagement unit, the second (of two) repositionable engagement units, the "flexible drive arm" or the "flex drive arm", "drive" indicating that the function of the element is to intermittently, e.g. after a set number of events, engage the second wheel so as to share the energy of rotation of the first wheel with the second wheel and to "drive" its rotation in conjunction with the first wheel.

In one aspect, the flex drive arm can be attached to or part of the first wheel. In some embodiments, the flex drive arm can be manufactured as a separate component and fastened onto the first wheel so as to facilitate its function, such as by glue, screws, tongue and groove, snap fit, heat staking or heat welding, or other similar or equivalent mechanism capable of achieving such an attachment. For example, a separate flex drive arm may have a tongue element capable of sliding into and along a groove in the surface of the first wheel such that the two elements may be fastened together. Alternatively, the first wheel flex drive arm may be heated and melted onto the first wheel. An advantage of the first wheel flex drive arm being integral to the main body of the first wheel is that it reduces the number of total components of the indicator apparatus and prevents the need for any type of fastening mechanism which could fail or otherwise interfere with the cooperation of multiple components. In one aspect, it may be useful to manufacture the flex drive arm as a separate component so as to facilitate slightly different positioning such that it allows a particularly designed indicator apparatus to fit within a defined space of a specific dispensing device.

The repositionable engagement unit intermittently engaging the second wheel can be a first wheel flex drive arm arranged annularly, or circumferentially, about the first wheel. The first wheel flex drive arm can be an arm, fastened at one end to the first wheel, but that protrudes freely from or separate from the first wheel at its opposite end. In one embodiment, the first wheel flex drive arm can extend from the side of the first wheel such that it remains in the same plane of the first wheel. In an alternative embodiment, the first wheel flex drive arm extends from the side of the first wheel but is torqued, twisted, or otherwise designed such that part or all of the first wheel flex drive arm from the point of attachment to the free end of the first wheel flex drive arm raises above, or falls below, the plane of the first wheel.

The repositionable engagement unit, when embodied as a first wheel flex drive arm arranged annularly about the first wheel, can be arranged such that from the point of its attachment to the first wheel to the tip of the arm, its length represents at least 1% of the overall circumference of the first wheel. That is, the amount of the overall circumference of the first wheel represented by the length of the first wheel flex drive arm can be at least 1%, at least 3%, at least 5%, at least 10%, at least 15% or in some aspects more, such as at least approximately 20%, at least approximately 25%, at least approximately 30%, at least approximately 35%, at least approximately 40%, at least approximately 45%, or at least approximately 50% of the overall circumference of the first wheel. According to one embodiment, the length of the first wheel flex drive arm represents between about 5% and 50% of the total circumference of the first wheel, such as about between 10 and about 45% or about 15 to about 40% of the total circumference of the first wheel.

The repositionable engagement unit responsible for intermittently, e.g. upon a certain number of events, engaging with the second wheel can be arranged within the indicator apparatus such that upon a set number of actuations or events, it engages with a positioning element which diverts the repositionable engagement unit from one path of motion to a second path of motion, the second path of motion being one in which the first wheel flex drive arm engages the second wheel.

A repositionable engagement unit can be a first wheel flex drive arm designed to engage with a positioning element on the base, the positioning element blocking a first path of motion of the first wheel flex drive arm and forcing a second path of motion of the first wheel flex drive arm, the second path of motion being one in which the first wheel flex drive arm engages with the second wheel. The repositionable engagement unit responsible for driving the rotation of the second wheel can remain disengaged from the second wheel unless it comes into contact with the positioning element of the base, such contact occurring only upon a set number of events. According to aspects, the set number of events is every $10^{th}$ event.

According to certain embodiments, to further facilitate the engagement of the repositionable engagement unit responsible for driving the rotation of the second wheel with the second wheel, the repositionable engagement unit further comprises a catch. A "catch" can be any type of wheel engagement element, such as one or more protrusions of any kind, e.g. a tab, knob, bump, tooth, or other such mechanism capable of being received by a complementary recession in one or more cooperating element(s). According to certain embodiments, the wheel engagement element or catch element of the repositionable engagement unit responsible for driving the rotation of the second wheel comprises one or more teeth. According to one embodiment, the wheel engagement element is a "driver catch", or second wheel driver tooth located on the flex drive arm of the first wheel.

According to certain embodiments, a flex drive arm of the first wheel drives the second wheel through engagement of the second wheel driver tooth with a latch mechanism on the second wheel. The latch mechanism of the second wheel can be a second wheel second set of teeth. The catch mechanism of the repositionable engagement unit responsible for driving the second wheel, e.g. the second wheel driver tooth, can have a rectangular, square, triangular or pyramid shape, a semi-circular, oblong, squircular shape, or have any type of trapezoidal, polygonal, or similar or equivalent shape which interacts with another element of the apparatus having a complementary shape or any shape that interacts with, e.g. a tooth of the second wheel latching mechanism having such a complementary structure. According to common embodiments, the second wheel driver tooth has a polygonal shape designed to be complementary to the shape of the second wheel latching mechanism, which can be, as will be described, a second set of teeth.

In some aspects the catch mechanism of the repositionable engagement unit responsible for driving the second wheel (e.g. a second wheel driver tooth on a flex drive arm attached to the inner wheel), can make a relatively loose contact with the latching mechanism on the second wheel, (e.g. the second wheel second set of teeth), upon every actuation, even when not being fully engaged with the latching mechanism such as that which occurs upon every set number of events. Such a relatively loose contact can be defined as contact sufficient to aid in holding or hold the inner wheel in a position preventing inadvertent rotation unless forced to rotate via an actuation (e.g. unless acted upon to rotate as driven by a trigger event), but that is not strong enough to prevent rotation of the first wheel independent of the second wheel during an actuation, as is the case for every actuation except for those wherein the repositionable engagement unit responsible for driving the second wheel, (e.g. flex drive arm) interacts with a positioning unit on the base forcing engagement of the unit with the second wheel latching mechanism and causing rotation of both the first and second wheels.

A catch on the repositionable engagement unit responsible for driving the second wheel, e.g. the second wheel driver tooth of the flex drive arm on the first wheel, aids in the stabilization of the first wheel, preventing its rotation when rotation is not needed or desired for accurate operation of the device.

A first wheel can further comprise an element which, under certain conditions, e.g. upon a certain number of events, makes contact with a repositionable engagement unit responsible for stabilizing the second wheel, to be described elsewhere herein, to modify its position. In one aspect, the element which can modify the position of the base flexible arm is a positioning element. A positioning element can be a deflector (which may be called a first wheel deflector).

The purpose of the positioning unit located on the first wheel, e.g. a first wheel deflector, is to intermittently, e.g. upon every set number of events, interact, make contact, or otherwise cooperate with the repositionable engagement unit responsible for stabilizing the second wheel, as will be described further herein, to release the second wheel from a stabilized position, freeing it to be capable of rotating with the first wheel. According to certain embodiments, the positioning unit on the first wheel, e.g. first wheel deflector, can be a fin, tab, protruding panel, or other similar or equivalent element which makes contact with, interacts with, or cooperates with, for example causes a deflection of, the repositionable engagement unit responsible for stabilizing the second wheel. The positioning element on the first wheel can have any shape capable of forcing the repositioning of the repositionable engagement unit which stabilizes the second wheel, such as rectangular, square, squircular, triangular, trapezoidal, any polygonal shape, or any similar or equivalent shape capable of causing the deflection of another element when the positioning element and the other element come into contact with one another.

According to some embodiments, the positioning element on the first wheel deflector is fin-shaped tab extending from the side of the first wheel having at least one side, for example a leading edge of the deflector of the first wheel ("leading edge" meaning that edge of the deflector which is in front as the first wheel is rotated) which is angled so as to facilitate smooth deflection of the repositionable engagement unit responsible for stabilization of the second wheel into which it comes in contact. As some designs may cause a catch or snag or otherwise may require additional force for the deflector to deflect the element or component into which it comes into contact, in one aspect the first wheel deflector is an element having an angled leading edge which first contacts the component to be repositioned such that when contact is made, pushing of the component is easily facilitated; as the first wheel deflector begins to slide past the component, the angle is designed such that as the first wheel deflector pushes past the component with which it has made contact, the component is pushed further and further away from the central axis of the first wheel.

In one embodiment, the repositionable engagement unit responsible for stabilizing the second wheel comprises an element which makes contact with the first wheel deflector causing a modification of position of the repositionable engagement unit. In one aspect this element is a positioning assistance element on the repositionable engagement unit responsible for stabilizing the second wheel. According to certain embodiments, as will be described elsewhere herein, the repositionable engagement unit responsible for stabilizing the second wheel is a flexible arm on the base and the positioning unit present thereon is a "stabilizer deflector" or base flexible arm deflector.

A flexible arm deflector can cooperate with a first wheel deflector such that upon every set number of events the first wheel deflector pushes or deflects the flexible arm via a flexible arm deflector. The deflector on the flexible arm can be angled such that when it comes into contact with the deflector on the first wheel, the deflector on the first wheel and the deflector on the flexible arm slide against each other, each being angled in opposite directions, leading them to slide against each other and as they do, the base flexible arm is pushed out and away from the base, releasing a wheel stabilization element at the end of the base flexible arm from the latch mechanism on the second wheel, freeing the second wheel to rotate with the first wheel.

The second wheel can take the form of a disc, ring, or any other suitable type of wheel-shaped member. The second wheel typically shares and rotates about the same longitudinal axis as the first wheel. In one aspect, the first wheel and the second wheel are concentrically positioned, rotate about the same longitudinal axis, and are oriented in the same direction. In one aspect, the second wheel takes the form of a ring and the first wheel (e.g. disc or ring shape) is sized and shaped for receipt within the second wheel; that is, the second wheel is positioned around or outside of at least a portion of the first wheel. The orientation and size relationship between the two wheels are discussed in detail elsewhere herein. As stated previously for sake of orientation, as used herein the "front" side or face of the first wheel is the side or face comprising visual communication elements, e.g. event indicators, to described elsewhere. The "back" side or face of the first wheel is the side or face comprising the latching mechanism. With regard to the second wheel, the "front" side is the side or face comprising event indicators, described elsewhere. The "back" side or face of the second wheel is the side of the wheel opposite the side with the event indicators.

A second wheel can comprise a latching mechanism, which engages with another element of the indicator apparatus, such as for example the repositionable engagement unit responsible for driving rotation of the second wheel, the repositionable engagement unit responsible for stabilizing the second wheel, or even more specifically, a catch element on either or both of those two components. Such a latching mechanism can be, for example, one or more insets or one or more protrusions shaped to receive, interact, cooperate or engage an element having a complementary shape or a shape suitable for and capable of engagement. In one aspect, the second wheel latch mechanism is a second set of teeth. In one embodiment, the second wheel teeth are oriented in an annular manner about the circular second wheel.

The second wheel latching mechanism, e.g. second wheel second set of teeth, can comprise any number of teeth, for example at least 2 teeth, at least 4 teeth, at least 6 teeth, at least 8 teeth, or at least 10 teeth, or at least 12 teeth or more, such as at least 14 teeth, at least 16 teeth, at least 18 teeth, or at least 20 teeth or more. According to one embodiment, the second wheel has at least 10 teeth, e.g. the second wheel has 12 teeth. The number of teeth of the second wheel determines how high of an event occurrence the indicator apparatus can register as, according to some embodiments, the second wheel dictates the larger units, e.g. the tens and hundreds place of a single, cooperatively presented event count (cooperatively presented with the demarcations on the first wheel, the first wheel presenting the ones unit of such a cooperatively presented number).

According to one embodiment, the latching mechanism of the second wheel is arranged annularly around the back side of the second wheel, that is the side or face of the second wheel opposite that comprising visual indicators for presenting a visual message to a user. The second wheel latching mechanism can comprise elements, e.g. teeth, which protrude outward from the back face of the second wheel. In one embodiment, each protrusion, or tooth, of the set of protrusions (e.g., teeth) exists independent from the next; that is, each rises directly from the face of the wheel and does not contain any element which joins one tooth to the next along any one side of any one tooth. In certain embodiments, there may be a unifying feature which joins one tooth to the next, for example a ridge or wall annularly encompassing the elements of the latching mechanism (e.g. teeth) from the outside of latching mechanism elements, the inside of the latching mechanism elements, between the elements of the latching mechanism elements, or any combination thereof.

In one embodiment, the latching mechanism of the second wheel is accessible to other components of the indicator apparatus from an outward direction moving inward. According to an alternative embodiment, the latching mechanism of the second wheel is accessible to other elements of the indicator apparatus from an inward direction moving outward. According to yet a further embodiment, the latching mechanism of the second wheel is accessible to other elements of the indicator apparatus from both an inward and an outward direction, either simultaneously or at different times during any one actuation of the indicator apparatus. The latching mechanism of the second wheel can be accessed from a position above the plane of the latching mechanism downward, toward the latching mechanism, e.g. toward the back surface of the second wheel. For example, in some aspects a repositionable engagement unit, e.g. a flexible arm, for example the repositionable engagement unit responsible for stabilizing the second wheel as is described elsewhere can flex toward the second wheel latching mechanism from an outward direction, flexing inward, toward the longitudinal axis about which both the first and second wheels rotate, to engage the latching mechanism of the second wheel. In aspects, a repositionable engagement unit, for example a repositionable engagement unit responsible for driving the second wheel as previously described (e.g. the a flexible drive arm on the first wheel) or other engagement device can flex toward the second wheel latching mechanism from an inward direction, flexing outward, away from the longitudinal axis about which both the first wheel and second wheel rotate, to engage the latching mechanism of the second wheel. In aspects, both such engagement mechanisms are used, either independently or simultaneously. One such engagement mechanism may be initiated, and one such engagement mechanism may be disengaged, substantially simultaneously.

The second wheel can be provided with an element capable of visually blocking the visual indicators present on the first wheel. The element can be any element capable of interfering with the visual display of event indicators present on the first wheel at a particular point in the indicator apparatus life cycle. In certain aspects, the element can be a protrusion, shutter, a flap, panel, tab, cover, screen, or other similar or equivalent element which prevents viewing of one or more visual indicators or demarcations of the first wheel. According to one embodiment, the second wheel of the indicator apparatus of the present invention comprises a shutter capable of blocking part or all of the event indicators being displayed by the first wheel.

According to certain embodiments, a material (e.g., drug) dispensing device in which the indicator apparatus resides comprises a status identifier in the form of a hole (e.g. an opening or a window) in its outer body through which the user can read the event indicators on the indicator apparatus. Such a status identifier (e.g., a window) can focus, limit, or highlight visual message communicated by the event indicator(s) on one or both wheels of the indicator apparatus. The shutter can serve to close off or otherwise block such a viewing window. The blocking of the viewing window can occur at a predetermined point, for example a predetermined point in the event occurrence cycle, for example after a certain number of events such as after the indicator apparatus has reached the end of its event registration cycle. For example, according to one embodiment, the second wheel shutter can close off viewing through the viewing window at the 'end of life' of the indicator apparatus, which typically corresponds to the point at which all events in a given event cycle, e.g. all doses of a medicament in a medicament dispenser, have been provided or when no full doses remain in a container holding a substance to be dispensed by a dispensing device housing the indicator apparatus. In one aspect, when used in a dispensing device, the blocking or closure of the window by the shutter on the second wheel may indicate to a user that no full doses, treatments, applications or applicable administrations of the substance held within the dispensing device remain.

In another aspect, the shutter can be printed, imprinted, carved, etched, pasted, scored, burned, or embossed to provide visual information in the form of numbers, words, letters, colors, shapes, symbols, pictograms or similar to indicate 'end of life' of the dispensed substance. For example, in one aspect the shutter can have an indicator therein which reads or indicates, "empty", "refill required", "0 remaining doses", "locked", or other similar message. Such a message could be in the form of words of any number of languages or could be a symbol, such as for example but not limited to an "X", a sad or unhappy face, an empty box or square, an empty circle, or other similar more universally recognizable symbol.

According to embodiments wherein the indicator apparatus comprises a second wheel having a shutter, it is likely that it will be used in the context of being incorporated into a dispensing device having an event indicator in the form of a viewing window, as these two elements function together to accomplish the goal of facilitating the viewing of, then limiting the view of, a visual message. In such embodiments, the indicator apparatus can be designed such that when the final dose is administered, instead of the first or first and second wheels rotating to provide a new message (e.g. a new event count) through the status identifier (e.g. viewing window), the second wheel rotates the shutter into place where it covers the viewing window. A first set of readable event indicators can be present on the first wheel while a second set of readable event indicators can be present on the second wheel. The event indicator(s) can be printed, imprinted, carved, etched, pasted, scored, burned, embossed or otherwise marked on the front side of the first wheel as previously defined to provide visual information to a user. The readable event indicators on the first wheel can be in the form of one or more digits, numbers, letters, words, shapes, colors, symbols, pictograms or similar such communicative means alone or in any combination capable of communicating a message to a user. The event indicators can be used to convey any type of information to a user of the indicator apparatus or dispensing device in which the indicator apparatus may reside. Event indicators can be shapes, colors, symbols, pictograms or the like rather than alphabetic, numeric, or alpha-numeric. When event indicators are numeric characters and provide a quantification of event occurrences, e.g. event "counts", the indicator device may be most accurately described as an event counting device (e.g. a "treatment counter" for a medical treatment device).

According to certain embodiments, the event indicator(s) on the first wheel comprise numerals. According to further embodiments, the numerals can indicate a numeric status of events to the user. According to one embodiment, the numeric indicator of the first wheel can, alone or in conjunction with further indicators provided by cooperating with event indicators on the second wheel as will be discussed further herein, provide information such as for example the total number of times the indicator device has been actuated (e.g. the number of events registered or, e.g. doses administered by the dispensing device) or the total number of remaining events the indicator device is capable of registering (e.g. the number of remaining doses in the dispensing device).

In some aspects, the second wheel of the device counter may comprise a second set of one or more event indicators capable of sending a visual message to a user. Such event indicators may be of the same or similar design to those of the first wheel. Alternatively, such event indicators on the second wheel may be different from and convey a different message than, that of the first wheel. According to certain embodiments, the event indicators of the first wheel can be presented to the user independent of any other messaging, the message conveyed by the first wheel alone being sufficient to communicate to the user, such as in an exemplary embodiment wherein the indicator apparatus is housed within a medicament dispenser the first wheel alone can be capable of indicating, e.g., the number of doses having been dispensed by the dispensing device, the number of doses remaining in the dispensing device, a warning about the level or number of doses remaining or the number of doses dispensed, a reminder to the user to refill a prescribed medicament dispensed by the dispensing device (e.g. medicament dispenser) within a given period of time, or any message aiding the user in the use of the substance dispensed by the dispensing device housing the indicator apparatus delivered by a numeric, alphabetic, symbolic, color-coded, or other type of visual event indicator as previously described. This can also be true for the event indicators on the second wheel, the event indicators on the second wheel being capable of presenting to the user a message independent of any other messaging present on the first wheel.

According to some embodiments, the messaging of the first wheel can cooperate with messaging of the second wheel to expand the capabilities of the device to provide visual messaging to a device or apparatus user. In such circumstances, the first and second wheels of the indicator apparatus are capable of aligning and/or align with one another in such a manner and location such that a visual message can be presented to the user, each wheel presenting an independent message alone, or a single message being presented by their cooperation with one another. In some aspects, when presenting a single message together in cooperation, such as numerals on the first wheel (e.g. "9") aligning with numerals on the second wheel (e.g. "10"), an expanded communication may be passed to the user, in this example a larger number is presented (e.g. "109"). Such cooperative ability can allow, for example, the indicator apparatus to present the status of a much larger number of events than what is feasible to present using a single wheel.

According to some embodiments, the visual information presented by the event indicators present on the first wheel and second wheel may be present in different color combinations if desired. Such a modification of visual information can be helpful, for example, for further indicating to the user the status of remaining doses. For example, in one embodiment wherein the indicator apparatus is housed within a medicament dispenser, upon initial use with a new medicament container comprising 120 doses of medicament, when 120-30 doses are remaining, the "12"-"3" (that is the numerals 12, 11, 10, 9, 8, 7, 6, 5, 4, and 3) of the second wheel having the numerals 12, 11, 10, 9, 8, 7, 6, 5, 4, 3, 2, 1, and optionally 0, may be colored green, indicating that at least 30 full doses remain in the medicament dispenser. Upon the 30$^{th}$ dose, when the indicator apparatus increments from having 30 doses remaining to 29, the "2" on the indicator apparatus may be colored orange, indicating to the user that less than 30 doses of medicament remain. The change in color can be a reminder to the user to give consideration of the status of remaining medicament some consideration. Further, when the 20$^{th}$ dose of medicament is administered and the indicator apparatus increments from having 20 doses remaining to 19, the "1" on the indicator apparatus (as indicated by the second wheel) may be colored red, indicating to the user that less than 20 doses remain and signaling consideration to the user of, e.g. pursuing a prescription refill as the indicator apparatus is indicating that the medicament container is reaching an end of life (an exhaustion of remaining doses); that is, the dispenser is nearing empty.

When presenting a message together in cooperation, the two wheels can align their respective messages both with one another as well as with a status identifier if present, e.g. a location of the dispenser body where the message is visible through a status identifier window. According to certain embodiments, when presenting a message together in cooperation, the two wheels present a visual message to a user which is clearly visible and easily interpreted.

According to some aspects, the visually displayed message, e.g. a number having 2 or more digits, can have digits which are properly aligned so as not to provide confusion for the user. In some aspects the digits can remain stable when, for example, the indicator device is shaken or otherwise moved or handled, therefore the first and second wheels can remain securely locked in place when not completing an actuation. The event indicators can be of such a size so that they are readable by a user and are in a form that is readable to a user. As such, the use of symbols may be appropriate for use in a population of users not sharing the same spoken and/or written language. Alternatively, multiple indicator apparatuses, or minimally the first and second rings of a indicator apparatus, can be manufactured such that they comprise event indicators easily interpretable to those of various spoken or written language, such as for example, indicator apparatuses presenting modern Arabic or Hindu-Arabic numerals, simple or complex Chinese numerals or numerals of any other of the written language of the world. In some aspects, the event indicators may be in braille and may be presented in such a manner so as to be accessible for the user to read by touch.

The event-related indicator apparatus of the present invention can have two or more wheels, such as 2 wheels, 3 wheels, 4 wheels, 5 wheels, 6, wheels or even more, such as 7 wheels, 8 wheels, 9, wheels or even 10 wheels or more than 10 wheels. The mechanisms described herein for their operation could be applied to any number of wheels, the mechanisms simply being present in greater quantity to accommodate for the increased number of wheels. According to certain wherein the indicator apparatus comprises more than two wheels, as is the case in embodiments wherein the indicator apparatus comprises two wheels, all wheels are concentrically aligned, share a longitudinal axis of rotation, and are oriented in the same direction.

Wheels associated with teeth can have any number of teeth. The number of teeth of any single wheel may be spaced the same as or differently from the teeth of any one or more other wheels within the indicator apparatus. The spacing may be determined based on the relationship between two or more wheels and the quantity of events which the indicator apparatus is designed to be capable of registering. Generally, the more inwardly positioned a wheel is relative to a shared axis of rotation, the fewer teeth it will have; as the wheels progress outward, around more inwardly positioned wheels, generally they will have a greater number of teeth.

According to certain embodiments, the size of the wheel and the spacing of the teeth can be anything suitable for operation of indicator apparatus. Typically, an inner or first wheel has 10 teeth and a second wheel has at least 12 teeth. In common embodiments, a third, fourth, fifth, or sixth wheel or more will each progressively have more teeth than the one before.

Typically, the latching mechanism present on wheel three and each subsequent wheel included in the apparatus can comprise a latching mechanism similar to or the same as the second wheel. However according to certain embodiments, the latching mechanism can vary so long as its ability to operatively cooperate with other components of the indicator apparatus are not compromised and functionality of the device is maintained.

Each wheel can be of any suitable diameter or thickness and can have any suitable positioning in the device (or larger device/system in which it is incorporated). According to certain embodiments, a first wheel is positioned within, e.g. in the center of, all other wheels. The second wheel is positioned such that its outer or front face has a widest diameter wider than the front face of the first wheel having visual indicators thereon and is positioned such that the wheels are capable of aligning one or more indicators on their respective sets of event indicators so as to be capable of presenting a combined message as previously described. A third wheel, if present, can be positioned such that its outer or front face has a widest diameter wider than the front face of the second wheel having visual indicators thereon and is positioned such that the first, second, and third wheels are capable of aligning one or more indicators on their respective sets of event indicators so as to be capable of presenting a combined message as previously described. As a fourth, fifth, sixth, or more wheels are added, their positioning would continue to be such that their outer or front face has a widest diameter wider than the front face having visual indicators thereon of the wheel positioned within it and is positioned such that the wheels are capable of aligning one or more indicators of their respective sets of indicators so as to be capable of presenting a combined message as previously described. In some aspects, all wheels present in the indicator device comprise a set of event indicators. In some aspects, all wheels present in the indicator device rotate about a concentric longitudinal axis of rotation. In some aspects, all wheels are oriented in the same direction.

In some embodiments, the total diameter of an inner and an outer wheel can be the same. However as is described herein, one or more wheels often can have areas of a face/side carved away so as to allow for nesting of another wheel about, around, or inside it. Therefore, when speaking about the diameters of multiple wheels, the widest diameter of an outer wheel is the widest part of the wheel having visual event indicators, and the face of the inner wheel having visual event indicators is that plane of the wheel face comprising the event indicators such that the outer wheel encircles the inner wheel, the event indicators of the outer wheel being outside the event indicators of the inner wheel relative to the shared axis of rotation of both wheels.

According to one embodiment, the event-related indicator apparatus of the present invention comprises two wheels: a first wheel and a second wheel. The widest diameter of the second wheel can therefore typically be greater than the face of the first wheel having event indicators on it. For example, the diameter of the second wheel can be at least 5% greater than that of the first wheel face comprising event indicators, for example at least about 10% greater, at least about 15% greater, at least about 20% greater, about 25% greater, or even about 30% greater or more, such as approximately 35% greater, approximately 40% greater, approximately 45% greater, approximately 50% greater, approximately 55% greater, or even approximately 60% greater or more, as in about 65% greater, about 70% greater, about 75% greater, about 80% greater, about 85% greater, about 90% greater, or even about 95% greater or more than that of the first wheel face.

The first and second wheels can rotate about a longitudinal axis which passes through the center of the first wheel. According to certain embodiments, the first wheel is sized and shaped such that it can be received within the second wheel, the second wheel having a hole or correspondingly-shaped cut- or carved-out area for receiving the first wheel. For example, the first wheel can in some embodiments fit completely within a cut-out hole in the center of the second wheel. Alternatively, the first wheel may fit partly within an area of the second wheel having been carved out, such as part of the thickness of the second wheel is carved out so as to create a "nest" or area such that the first wheel can sit within it. Such a carved-out area can be on the front/outer surface of the second wheel, e.g. the surface which can further comprise event indicators. Such a carved-out area can alternatively be on the back side or back surface or inside surface of the second wheel, that is the surface which does not comprise event indicators. Such a carved-out area may or may not comprise an area wherein the carving goes completely through the second wheel so as to create a hole. Such a carved out area can comprise at least 0.01% of the second wheel thickness (depth), such as for example about 0.01% of the second wheel depth, about 0.05%, about 0.1%, about 0.5%, about 1%, about 5%, about 10%, about 15%, about 20%, or at least about 25% of the second wheel thickness, as in approximately 30%, approximately 35%, approximately 40%, approximately 45%, or even approximately 50% or more, as in about 55%, about 60%, about 65%, about 70%, or about 75% or more, for example approximately 80%, approximately 85%, approximately 90%, approximately 95% or even more, such as about 96%, about 97%, about 98%, about 99%, or even about 99.5% or even 100% of the thickness of the second wheel has been removed. In an embodiment where the second wheel has an area 100% carved out to fit the first wheel, there is a hole in the second wheel in which all or at least part of the first wheel is configured to fit. When fit within the second wheel, the first wheel and second wheel are free to rotate unless intentionally impeded by other elements of the event indicator. In some aspects when fit within the second wheel, the first wheel and second wheel are free to rotate independently from one another or also or alternatively are capable of rotating together when directly engaged with one another as facilitated by specific components of the event indicator as described herein.

According to some embodiments, the second wheel has an area carved out so as to create a nesting position for the first wheel and the thickness of the first wheel is such that when nested within the second wheel, at least one outer surface of each is coplanar. If the second wheel has an area carved out so as to create a nesting position for the first wheel within the second wheel, the thickness of the first wheel may be equivalent to the depth of the carved-out area. That is, for example, if the second wheel has a region in which 25% of its thickness has been removed, the thickness of the first wheel may be 25% of that of the second wheel. For example, if the second wheel has a region in which 50% of its thickness has been removed, the thickness of the first wheel may be 50% of that of the second wheel such that when nested within the second wheel, the outer surfaces of the first wheel and the second wheel can be flush and coplanar.

The carved-out area can represent an area of at least 1% of the surface area of one side of the second wheel's surface area. According to certain embodiments, the carved out area can comprise at least about 1% of the second wheel surface area, such as at least about 5%, at least about 10%, at least about 15%, at least about 20%, at least about 25%, at least about 30%, at least about 35% or more, such as at least approximately 40%, at least approximately 45%, at least approximately 50%, at least approximately 55%, at least approximately 60%, at least approximately 65%, or at least approximately 70% of the second wheel surface area, as in at least about 75%, at least about 80%, at least about 85%, at least about 90%, or at least about 95% or more. In such embodiments where the carved out area represents a percentage of the total surface area of one side or surface of the second wheel, the diameter of the plane of the face of the first wheel comprising event indicators can be such that it matches the diameter of, or is just slightly smaller than, the diameter of the carved out area, such that when the first wheel is nested within the second wheel, it fills the carved-out area while being able to freely rotate without impedance due to friction with the edges of the carved out area of the second wheel.

According to one embodiment, the first wheel is concentrically positioned within the second wheel. According to one embodiment, the first wheel is concentrically positioned within the second wheel such that less than 95% of the surface areas of the two wheels overlap, such as for example less than about 95%, less than about 90%, less than about 85%, less than about 80%, less than about 75%, less than about 70%, less than about 65%, or less than about 60% overlap, such as less than approximately 55%, less than approximately 50%, less than approximately 45%, less than approximately 40%, less than approximately 35%, less than approximately 30%, as in less than about 25%, less than about 20%, less than about 15%, less than about 10%, or less than about 5% or even less of the surface areas of the first wheel and the second wheel overlap.

In some embodiments, the diameter of the first wheel is less than that of the second wheel. At a minimum, in typical embodiments the diameter of the plane of the face of the first wheel comprising event indicators is less than the widest diameter of the second wheel. For example, the widest diameter of the first wheel, or also or alternatively the diameter of the plane of the face of the first wheel comprising event indicators, can be about 5% or more smaller than that of the widest diameter of the second wheel, for example about 5% smaller, about 10% smaller, about 15% smaller, about 20% smaller, about 25% smaller or about 30% smaller, such as for example approximately 35% smaller, approximately 40% smaller, approximately 45% smaller, approximately 50% smaller, approximately 55% smaller or even approximately 60% smaller or more, as in about 65% smaller, about 70% smaller, about 75% smaller, about 80% smaller, about 85% smaller, about 90% smaller, or even about 95% smaller or more. The first and second wheel may have overlapping, a concentric and/or co-planar, orientation.

In one embodiment, the second wheel is assembled over the first wheel in an overlapping configuration such that the front face of both the wheels are co-planer and form a common display and/or counter zone for providing a visual communication to a user. In such an embodiment, at least about 1% (e.g., at least about 1.5%, at least about 2%, at least about 2.5%, at least about 3%, or at least about 5%) of the surface area of one surface of the first wheel is carved away so as to create an "edge" or "lip" for the second wheel to sit within or on, such that the outer surface of the first wheel and the outer surface of the second wheel are coplanar when the second wheel is situated in the edge. In such a configuration, the central area of the outer surface of the first wheel protrudes into and fills a space or hole in the middle of the second wheel.

According to some embodiments, the first wheel has an area which is recessed or "carved away", e.g. a depressed area or area of less thickness, so as to create a nesting position for the second wheel and the thickness of the second wheel is such that when nested over the first wheel, at least one outer surface of each is coplanar. Said another way, if the first wheel has a recessed area so as to create an area of decreased thickness and thus creating a nesting area for positioning of the second wheel over the first wheel, the thickness of the second wheel may be equivalent to the depth of the nesting area. That is, for example, if the first wheel has a region in which about 25% of its thickness has been removed, the thickness of the second wheel may be 25% of that of the first wheel. To further exemplify this point, if the first wheel has a region in which 50% of its thickness has been removed, the thickness of the second wheel may be 50% of that of the first wheel such that when nested over the first wheel, the front/outer surfaces of the first wheel and the second wheel are flush and coplanar.

A nesting (e.g. carved out) area can represent an area of at least 1% of the surface area of one side of the first wheel's surface area. In some aspects, the side of the first wheel which is removed is the outer surface of the first wheel which can further comprise event indicators capable of providing a visual message to a user. According to certain embodiments, the recessed area can comprise at least about 1% of the first wheel surface area, such as at least about 5%, at least about 10%, at least about 15%, at least about 20%, at least about 25%, at least about 30%, at least about 35% or more, such as at least approximately 40%, at least approximately 45%, at least approximately 50%, at least approximately 55%, at least approximately 60%, at least approximately 65%, or at least approximately 70% of the first wheel surface area, as in at least about 75%, at least about 80%, at least about 85%, at least about 90%, or at least about 95% or more of the first wheel surface area can be removed or carved away. In such embodiments where the recessed area represents a percentage of the total surface area of one side or surface of the first wheel, the inner diameter of a ring-shaped second wheel can be such that it matches the diameter of, or is just slightly smaller than, the inner diameter of the carved out ring area encircling one plane of the first wheel, such that when the second wheel is positioned over the first wheel, it covers the recessed area while being able to freely rotate without impedance due to friction with the edges of the carved out area of the first wheel.

In some embodiments, the second wheel is located over the first wheel in an overlapping configuration, such that the front face of both the wheels are co-planer and form a common display and/or counter zone for providing a visual communication to a user. In such an embodiment, at least about 1% of the surface area of one surface of the first wheel can be recessed or carved away so as to create a depressed ring or "edge" for the second wheel to sit within or on, such that the outer surface of the first wheel and the outer surface of the second wheel are coplanar when the second wheel is situated in the edge. In such a configuration, the central area of the outer surface of the first wheel can protrude into and fill a space or hole in the middle of the second wheel.

According to one embodiment, the second wheel is concentrically positioned over the first wheel. According to one embodiment, the second wheel is concentrically positioned over the first wheel such that less than 95% of the surface areas of the two wheels overlap, such as for example less than about 95%, less than about 90%, less than about 85%, less than about 80%, less than about 75%, less than about 70%, less than about 65%, or less than about 60% overlap, such as less than approximately 55%, less than approximately 50%, less than approximately 45%, less than approximately 40%, less than approximately 35%, less than approximately 30%, as in less than about 25%, less than about 20%, less than about 15%, less than about 10%, or less than about 5% or even less of the surface areas of the first wheel and the second wheel overlap.

The diameter of the second wheel is typically greater than that of the first wheel. In some embodiments, the widest diameter of the second wheel is wider than the widest diameter of the plane of the face of the first wheel comprising event indicators. For example, the diameter of the second wheel can be about 5% or more greater than that of the first wheel, for example about 5% greater, about 10% greater, about 15% greater, about 20% greater, about 25% greater or about 30% greater, such as for example approximately 35% greater, approximately 40% greater, approximately 45% greater, approximately 50% greater, approximately 55% greater or even approximately 60% greater or more, as in about 65% greater, about 70% greater, about 75% greater, about 80% greater, about 85% greater, about 90% greater, or even about 95% greater or more. The first and second wheel may have overlapping and/or concentric and/or co-planar, orientation.

In some embodiments, the first (inner) and the second (outer) wheels are concentric and coplanar; that is, the first wheel and the second wheel are arranged concentrically and share one surface at about the same level. In another embodiments, the first wheel and the second wheel are concentric and non-co-planar, that is the first (inner) and second (outer) wheels are arranged concentrically and at significantly different levels.

The first (e.g. inner relative to the axis of rotation) and second (e.g. outer relative to the axis of rotation) wheels can have overlapping, a concentric and/or co-planar, orientation. According to one embodiment, the second wheel is assembled over the first wheel in an overlapping configuration such that the front face of both the wheels are co-planer and form a common display and/or indicator zone. In one aspect, the outer faces of the first wheel and the second wheels exist predominately, completely, or almost completely (80%, 90%, 95% or more), on the same plane.

In some embodiments, the first wheel and the second wheels are concentric and have outer surfaces which are coplanar; that is, the first wheel and the second wheel are arranged concentrically and at about the same level (e.g. have faces on about the same plane). In another embodiments, the first wheel and the second wheel are concentric and have one or more surfaces which are non-co-planar. In one aspect, the first wheel and the second wheel are arranged concentrically and one or more of the outer surface or the back side of the first and/or second wheels exist on significantly different planes. According to one embodiment, the outer surfaces of the first and second wheels are essentially coplanar, while the back side or back surface of the first and second wheels are non-coplanar, as in, e.g., the circular boss of the first wheel can protrude or extend outward from the back surface of the first wheel and/or the second wheel is positioned on top of the first wheel such that the back of the first wheel, not inclusive of the boss, and the back of the second wheel are approximately parallel but non-coplanar.

In one embodiment, the first wheel and the second wheel can be arranged to rotate in the same direction, for example both wheels rotating in a clockwise direction when called upon or appropriately engaged for rotation, e.g. during an actuation of the actuation means, e.g. the actuator. In one aspect the same direction may be clockwise. In another aspect the direction may be counter-clockwise. In certain embodiments, the first wheel and the second wheel may be arranged such that they rotate in opposing directions, for example one wheel rotating in a clockwise manner and one rotating in a counter-clockwise direction. According to certain embodiments, each wheel is maintained in a stationary position unless conducting a rotation as triggered by an actuation.

The wheels of the indicator apparatus can have any suitable relationship that allows for effective operation of the indicator apparatus. In some embodiments, two or more wheels can share the same orientation, e.g. their front faces facing in the same direction, but may not share an axis of rotation. In some embodiments, two or more wheels can be coaxial, that is, share the same axis of rotation, but not be concentrically aligned. In some embodiments, two or more wheels can be coaxial and concentrically aligned. According to certain embodiments, the two wheels can be co-axial along the same longitudinal axis; longitudinal axis being an axis that defines an axis that passes from the front of an object (e.g. from the side of the wheels having the event indicators) to the back. According to some embodiments, the two wheels are concentrically aligned, are coaxial around a shared longitudinal axis of rotation, and are oriented in the same direction.

Devices of the invention can further comprise a means for securing (immobilizing) and conditionally (e.g., after occurrence a set number of events or set type of event), freeing the second wheel to allow it to be driven to rotate in conjunction with the first wheel. Any suitable means for stabilizing a second wheel or second member can be used for immobilizing the second wheel. Such a stabilization means can be any suitable means, e.g. any unit, element, or component capable of being in a position to interact with, contact, or otherwise engage with, or be disengaged from, the second wheel and is movable from one position to another. For example, a stabilization means can be a repositionable arm, a selective switch, a movable hook, catch, latch, or other similar or equivalent mechanism for engaging or disengaging the second wheel according to certain conditions and when engaged, stabilize its position such that it cannot rotate.

The indicator devices of the invention can comprise a base component that typically houses and/or aligns and/or supports other components. In cases where the base component contains/houses other components it may also be referred to as a "housing." A base will typically at least partially support one or more wheels and can, in certain embodiments, comprise other elements of the indicator apparatus which cooperate with one or more of the one or more wheels to effectively operate the indicator apparatus. In one aspect, a base component aids in or is responsible for operably positioning one or more indicator members/wheels in workable orientation and/or provides one or more supporting elements contributing to the successful and accurate operation of indicator apparatus. According to some embodiments, the first wheel and/or the second wheel reside at least partially within the base. In one embodiment the base has a diameter greater than that of the first wheel. Also or alternatively, in one embodiment the base has a diameter greater than that of the second wheel. Also or alternatively, in one embodiment, the base has a diameter greater than both the first and second wheel. A base can mount, orient, or otherwise locate a first wheel and the second wheel in position relative to one another while also allowing both wheels to rotate when free. The base can comprise elements which cooperate with both the first wheel and the second wheel and stabilize or otherwise improve operation of such elements. According to certain embodiments, the base of the indicator apparatus serves to hold the first and second wheels in position relative to one another and in such an orientation within the indicator apparatus base that the elements of the first wheel, second wheel, and base which need to cooperate, interact, or otherwise engage with one another are in proper alignment for effective functioning of the indicator apparatus.

A base component ("base") can comprise or be in the form of a frame, housing, platform, or similar or equivalent element or structure, wherein the first wheel is held in place for operation, the second wheel is held in place for operation, and the first and second wheels are held in place for operation relative to one another and to one or more elements of the base such that all components are able to cooperate to successfully operate the indicator apparatus. A base can have any suitable size and shape with respect to its function, e.g., holding wheel components, including a circular, square, squircular, rectangular, generally triangular, polygonal, or trapezoidal shape, or a shape that is generally one of these shapes. In one aspect, the base is generally circular in shape however can have protruding element operating to aid in securing or fastening the indicator apparatus to a larger device in which it is bound or held, which typically extend outward and away from the generally circular body.

In some embodiments, a base can comprise one or more securing or fastening means responsible for securing or fastening the indicator apparatus to a larger device, e.g., a material dispensing device, such as a MDI. Such a securing/fastening means can be or comprise any means suitable for holding the indicator apparatus in position during use of the use of the device. In some aspects, the means of securing or fastening the indicator apparatus to a larger device can be mounting holes, a clip, a tongue-and-groove mechanism, snap fit, heat staking or heat welding, or other similar or equivalent element which would allow for securely fastening the indicator apparatus to the device in which it is used. A fastening means can align indicators, wheels, and/or other components. In one embodiment the fastening element is one or more mounting holes on the base used to mount the counting device, e.g. using screws or pins separate from or connected to the body of the dispenser, to the body of the dispensing device.

A base can comprise a bore or hole to mount and/or position (locate) the first wheel. The bore or hole in a base can, e.g., aid in securing the first wheel in a position such that the elements of the first wheel can effectively cooperate with elements of the base (e.g., as needed for successful operation of the indicator apparatus) or other elements of the device or associated device(s). Also or alternatively, such a bore or hole (or a different hole/bore in the base) can, in some aspects, be used to position the second wheel. A bore/hole can be located in any suitable position, but typically will be centrally located. Typically, the base will comprise a single bore, though the base can incorporate 2, 3, 5, 10, or more bores. In some aspects, the base also or alternatively comprises a raised rim, edge, lip, or similar or equivalent element which aids in or provides the positioning of the second wheel, the second wheel sitting inside of a rim, edge, lip or similar or equivalent element of the base so as to hold it in position while still allowing it to rotate freely. A bore or hole in the base can allow insertion/passage of a boss, such as for example a boss on the first wheel, to secure a component e.g. the first wheel, to the base yet allow the component, e.g. the first wheel, to rotate freely. According to some embodiments, the base comprises two or more mounting holes, e.g., at least 3 mounting holes, or even more, such as 4 or about 5 mounting holes, or more, that serve as part of a fastening system. According to one embodiment, the base comprises 2 mounting holes which receive pins present on, and extending from, the body of an associated dispensing device. In some aspects, pins extending from a dispensing device body can slide through the mounting holes present on the indicator apparatus, e.g. present on the indicator apparatus base, which serve to hold the device counter securely in place during dispensing device operation.

A base can define the longitudinal axis of rotation of the first and second wheels of the indicator apparatus by, e.g., maintaining the position of the first and second wheels such that they share a common longitudinal axis of rotation. In one aspect, the axis is concentric. In some aspects, the first and second wheels also share a common orientation, the front faces of each wheel both being oriented in the same direction. The first and/or second wheel(s) can also or alternatively be mounted/positioned in such a manner so as to hold them in place but not prevent their rotation at the times they are required to rotate, e.g. during an actuation of the actuation means, e.g. the actuator. According to a particular embodiment, the base can maintain secured positions of the first wheel and the second wheel by a snap-fit or push-fit assembly of the first and/or second wheel(s) and the base.

According to one embodiment, a further function provided by the base is to prevent or aid in in the prevention of undesirable rotation of the second wheel, e.g., by including an element to hold (or aid in holding) the second wheel in position until such time that it is freed for rotation with the first wheel. In certain embodiments, this can be a repositionable engagement unit. In certain embodiments, the repositionable engagement unit can take the form of a repositionable and/or flexible arm attached to the base (or that is a part of a base). According to certain embodiments, the base of the indicator apparatus comprises a repositionable engagement unit responsible for stabilizing the second wheel of an indicator apparatus comprising two wheels, engaging with an element of the second wheel under set conditions, e.g. upon some, many, substantially all, or all except for actuations occurring after or upon a set number of events, to prevent its rotation. According to certain embodiments, the element of the base engages with the latching mechanism of the second wheel. In some aspects, the repositionable engagement unit is a flexible arm on the base. In embodiments where a repositionable engagement unit responsible for driving the rotation of the second wheel is an element of the first wheel and in the form of a flexible arm, the term "flex drive arm" or "flexible drive arm" can be used. Such an arm typically "drives" movement of the second wheel in operation of the device. In an embodiment where a repositionable engagement unit responsible for stabilizing the second wheel is an element of the base and in the form of a flexible arm, the terms "flex arm" or "flexible arm" may be used, as such an arm component does not "drive" the movement of any other component but instead engages with another component (the second wheel) in order to keep it stable and to prevent its rotation.

According to one embodiment, the repositionable engagement unit responsible for stabilizing the second wheel is a flex arm on the base capable of being in a stabilizing and a non-stabilizing position relative to the second wheel according to certain conditions. In such an embodiment, the flex arm on the base can be arranged annularly or circumferentially about the base. The base flex arm can be an arm, fastened at one end to the base, but that protrudes freely from or separate from the base at its opposite end. In one embodiment, the base flex arm extends from the side of the base such that it remains in the same plane of the base. In an alternative embodiment, the base flex arm extends from the side of the base but is torqued, twisted, or otherwise designed such that part or all of the base flex arm from the point of attachment to the free end of the flex arm raises above, or falls below, the plane of the base.

According to some aspects, the base flex arm, from the point of its attachment to the base to the tip of the arm, can be of a length such that it represents at least 1% of the overall circumference of the base. That is, the amount of the overall circumference of the base represented by the length of the flex arm can be at least about 1%, at least about 3%, at least about 5%, at least 10%, at least 15% or in some aspects more, such as at least approximately 20%, at least approximately 25%, at least approximately 30%, at least approximately 35%, at least approximately 40%, at least approximately 45%, or at least approximately 50% of the overall circumference of the base. According to one embodiment, the length of the base flex arm represents between about 5% and 50% of the total circumference of the base, such as between about 10% and about 45% or about 15 to about 40% of the total circumference of the base.

In some aspects, the flexible arm on the base has a further element aiding in the engagement of or with the latching mechanism of the second wheel. In some aspects, the element which engages with the second wheel latching mechanism is a wheel stabilizing element. In some aspects the wheel stabilizing element is located at the end of the flexible arm of the base. The wheel stabilizing element of the base flex arm can be any element capable of interacting with, contacting, or otherwise engaging the latching mechanism of the second wheel such that it holds the second wheel in a stable position and prevents its rotation. The wheel stabilizing element can be a tab, tooth, pawl, or other similar or equivalent element protruding from the end of the base flex arm which can engage with the latching mechanism of the second wheel. The shape of the wheel stabilizing element can be such that it complements the shape of the latching mechanism on the second wheel. In one aspect, the wheel stabilizing element is a pawl on the end of the base flex arm.

According to one embodiment, the repositionable engagement unit, e.g. the base flex arm, comprises a wheel stabilizing element, e.g. a pawl, and an element which can contact the positioning element on the first wheel to cause a modification of position of the base flexible arm. In some aspects, this position-modifying element is a base flexible arm deflector. In some aspects, the base flexible arm deflector is integral to the base flexible arm design. The pawl on the base flex arm can prevent the reverse rotation of the second wheel by locking into the latch mechanism (e.g. teeth) of the second wheel unless and until deflected away from the latching mechanism of the second wheel via interaction of the positioning element on the first wheel and the flexible arm deflector on the base flexible arm, in which the contact of the two elements pushes the base flexible arm outward and away from the latching mechanism of the second wheel, disengaging the pawl from the second wheel latching mechanism, hence freeing the second wheel to rotate.

In embodiments comprising a base flex arm, the base flex arm may not flex or deflect until a positioning unit, e.g., a deflector on the first wheel, contacts a base flex arm or a deflector on the base flex arm. In such an embodiment the device can be configured so that upon most or nearly all actuations of the indicator apparatus, the second wheel is held in place by a base flex arm pawl while the first wheel is free to rotate and to register an incremental event upon an actuation. The base flex arm can be intermittently, e.g., upon a set number of actuation events, deflected by the first wheel deflector, the base flex arm being deflected outward and away from the longitudinal axis about which the first and second wheels rotate. Such events can occur every set number of actuations, e.g., every ten actuations. Upon the tenth actuation, the first wheel deflector can push or deflect the base flex arm via the base flex arm deflector. According to certain embodiments, the base flex arm deflector can be angled such that when it comes into contact with the first wheel deflector, the first wheel deflector and the base flex arm deflector slide against each other, each being angled in opposite directions, such that when in contact, they slide against each other and as they do, the base flex arm is pushed out and away from the center of base, that is out and away from the latching mechanism of the second wheel, releasing the pawl on the end of the base flex arm from the latch mechanism (e.g. teeth) of the second wheel, freeing it to rotate with the first wheel.

According to one embodiment, the deflection of the base flex arm provides relief of the second wheel for the incremental movement of the second wheel by removing the wheel stabilizing element (e.g. pawl) from within the latching mechanism (e.g. teeth) of the second wheel, thereby unlocking it and freeing it for one increment of rotation.

According to certain embodiments, the base may further comprise a positioning element which modifies the motion of the repositionable engagement unit responsible for driving the rotation of the second wheel. The repositionable engagement unit responsible for driving the rotation of the second wheel can be a first wheel flexible drive arm. The positioning element on the base can be capable of preventing the deflection of the repositionable engagement unit responsible for driving the second wheel, e.g. the flex drive arm of the first wheel, which typically deflects inward, keeping the catch element on the repositionable engagement unit (e.g. first wheel flex drive arm) away from, or in a position incapable of engaging with, the latching mechanism of the second wheel. The positioning element on the base can be any element capable of making contact with the repositionable engagement unit responsible for driving the second wheel and modifying its position. In certain embodiments, the positioning element on the base is a tab, knob-like protrusion, bump, flap, panel, stud, or any similar or equivalent element which contacts the first wheel flex drive arm and disrupts its path as it rotates. In some cases, this element is a component referred to as a "stud."

In preventing the natural inward deflection of the repositionable engagement unit responsible for driving rotation of the second wheel (e.g. the first wheel flex drive arm), forced by the interaction of the first wheel flex drive arm with the positioning element of the base upon every set number of events, the first wheel flex drive arm, and more specifically the catch comprised thereon, is forced outward to engage with the second wheel latch mechanism, thereby resulting in the engagement of the second wheel with the first wheel and as the first wheel rotates, the second wheel is forced to rotate along with it, completing a single incremental movement of the second wheel about the shared first and second wheel axis of rotation upon each set number of actuation events.

According to embodiments, the first wheel flex drive arm flexes inwardly toward the longitudinal axis every time during the actuations of the actuator means unless it comes in contact with the positioning element of the base. The first wheel inward flexion keeps the first wheel flex drive arm catch away from, and thereby disengaged from, the second wheel, such that upon each actuation, the first wheel is free to rotate independently from the second wheel during most actuations. The inward flexion of the first wheel flex drive arm does not result in any motion of the second wheel. However, upon each set number of actuations of the actuator means, the first wheel flex drive arm comes into contact with the positioning element of the base. This contact allows the incremental movement of the second wheel by preventing the flexion of the first wheel flex drive arm away from the second wheel, instead forcing it outward toward the second wheel and forcing the engagement of the first wheel flex drive arm catch with the second wheel latching mechanism.

Although the devices of the invention described herein have been described and exemplified as comprising two indicator wheels (a first wheel and second wheel), in some aspects an indicator apparatus of the present invention comprises more than two indicator members (e.g., more than two indicator wheels), such as at least 3 indicator wheels, at least 4 wheels, at least 5 wheels, e.g., about 6 wheels or more, such as 7 wheels, 8 wheels, 9 wheels, or even 10 or more wheels. In such embodiments, each such second wheel (e.g., wheels 2, 3, and 4) can be associated with a "second wheel" stabilization element, e.g., a repositionable engagement unit, which can be attached to the base as a flexible arm, such that a base in such aspects may have two, three, four, five, six, seven, eight, or even nine repositionable engagement units in the form of flexible arms, each positioned about the base in a fashion similar to the embodiment described wherein the indicator apparatus has two wheels. In an embodiment wherein the indicator apparatus comprises two wheels, and the repositionable engagement unit responsible for stabilizing the second arm is attached to the base, the repositionable engagement unit responsible for stabilizing the second arm can be a flex arm attached to the base and is the only arm attached to the base.

Each indicator member, or indicator wheel, of an indicator apparatus of the invention can be of any suitable diameter and/or thickness. Typically the wheel/member diameter and thickness will allow for multiple wheels to operably interact with one another in the space provided. In embodiments wherein the indicator apparatus comprises more than 2 wheels, the first wheel can maintain the latching mechanism interacting with the actuation means to drive its rotation. According to embodiments, a first wheel is positioned in the center of all other wheels. The second wheel typically is positioned such that its outer or front face has a diameter at its widest point wider than the front face of the first wheel displaying event indicators and is positioned such that the wheels are capable of aligning one or more indicators on their respective sets of event indicators so as to be capable of presenting a combined message as previously described. A third wheel, if present, can be positioned such that its outer or front face has a diameter wider at its widest point greater than the diameter of the front face of the second wheel comprising event indicators and is positioned such that the first, second, and third wheels are capable of aligning one or more indicators on their respective sets of event indicators so as to be capable of presenting a combined message as previously described. As a fourth, fifth, sixth, or more wheels are added, their positioning would continue to be such that their outer or front face has a diameter at its widest point is wider than the front face comprising event indicators of the wheel positioned within it and is positioned such that the wheels are capable of aligning one or more indicators of their respective sets of indicators so as to be capable of presenting a combined message as previously described.

In an embodiment wherein the indicator apparatus comprises 2 wheels, the indicator apparatus comprises 2 repositionable engagement arms; a first to stabilize the second wheel and a second to drive the second wheel; and two positioning elements; one to position one of the repositionable engagement units to engage with and drive rotation of the second wheel, and one to position the repositionable engagement unit to free it from engagement with the second wheel to allow its rotation (e.g. position the repositionable engagement unit in a destabilizing position relative to the second wheel). For each additional wheel added to the apparatus, two additional repositionable engagement units are also typically added to the system, usually along with two additional positioning units to operably interact with the additional repositionable engagement units. According to embodiments where the indicator apparatus comprises three or more indicator wheels, the first, innermost wheel contains a latching mechanism to engage with the actuation means to receive the actuation energy from a trigger event. The first wheel can comprise one of the repositionable engagement units to engage with and drive the rotation of the second wheel upon a certain number of events when it makes contact with a positioning unit on the base. The first wheel can further comprise a positioning unit to make contact with one of the repositionable engagement units which can be an element of the base, when in contact disengaging the repositionable engagement unit from the second wheel, freeing it (or destabilizing it) and allowing it to rotate in conjunction with the first wheel. The second, third, fourth, fifth, sixth, and any successive additional wheel can take on one or more of the embodiments of what has previously described as the first wheel, that is it can comprise a drive arm to engage with an outer wheel, and can comprise a positioning element, to interact with a repositionable engagement unit responsible for stabilizing an outer wheel upon a set number of events.

In an embodiment where the indicator apparatus comprises three or more wheels, the base may comprise two or more repositionable arms, each responsible for stabilizing a wheel when engaged with a wheel, and being engaged with a wheel until such time that each comes into contact with a positioning element, in a manner similar to that already described for 2-wheeled devices.

Event status components of the invention can be associated with any additional types of devices, which can be, for example, liquid dispensers, pressurized aerosol dispensers, pre-filled containers or solid material dispensers such as, e.g., tablet, capsule, pellet, or agglomerate dispensers, and pumps, and such dispensers can include specifically medical dispensers such as inhalers, pens (e.g. injection pens or pre-filled pens), or syringes (e.g. pre-filled syringes), dispensers for intramuscular or subcutaneous delivery and the like, even in larger devices such as manufacturing equipment (e.g. food manufacturing or chemical manufacturing) or in jugs such as those containing an agrochemical such as a pesticide. Such a container can be designed for dispensing substance in a liquid, pressurized aerosol, or dry, e.g. granular or powder, form. It can find use in a device wherein dispensation or event related feedback is helpful or important but difficult to otherwise ascertain, such as in a medicinal/pharmaceutical inhaler of the type used in, e.g. bronchotherapeutic drug delivery, such as pressurized MDIs, or dry powder inhalers.

As described, the usefulness of event registering is not limited to the field of pharmaceuticals/medicine; e.g., an event indicator of the present invention may find particular use when incorporated into larger devices within in the food industry where a counting of dispensed foods may also be helpful, or for example in the chemical or agrochemical industries where, for example, the administration of, e.g., pesticide doses may be useful to track, or even in the petrochemical industry or manufacturing industry. In fact, the event-related indicator apparatus of the present invention can be used with any device which can benefit from a visual indication of the status of events, or substance held within, especially when such information may be otherwise difficult to discern and wherein there is a means and an opportunity for triggering an actuation means (e.g. actuator) of the indicator apparatus.

Therefore, while in some aspects the indicator apparatus can be manufactured as part of an integral part of a specific dispensing device, the indicator apparatus of the present invention can alternatively comprise an element which serves to fasten, connect, or otherwise attach it or otherwise associate it as a component or attached device to a larger device or system as a separate component thereof, or also or alternatively to provide one or more parts of a fastening system for fastening, connecting, or otherwise attaching the indicator apparatus to a larger device.

As mentioned previously, the indicator apparatus can be attached to a dispensing device (e.g. the body of a dispenser) via any component of the indicator apparatus which is capable of being held stationary without compromising the functionality of the indicator apparatus. According to one embodiment, the component of the indicator apparatus used to mount the indicator apparatus to the dispensing device in which it resides is the base component. The indicator apparatus can be fastened, mounted, or otherwise attached to and/or associated with a measuring, storage, or dispensing device, e.g., using mounting holes, a clip, a tongue-and-groove mechanism, snap fit, heat staking or heat welding, or other similar or equivalent mechanism which would allow for securely fastening the indicator apparatus to the device in which it is used. The fastening mechanism can be such that it maintains stability of position of the indicator apparatus, e.g. counting device, within the larger device. According to one embodiment, the fastening mechanism is one or more mounting holes in the indicator apparatus base used to mount, e.g. using screws or pins, the pins being separate or integral the body of the dispenser, to mount the device to the body of the dispenser device.

The various components of the inventive event measuring devices/components can be made from any suitable material or combination of materials. In some embodiments, all components of the indicator apparatus are made of a single material. According to alternative embodiments, one or more components can be made of different materials. In some aspects, one or more components of the indicator apparatus may comprise one or more materials. In some aspects, multiple elements of a single indicator apparatus component may comprise a material that differs from one or more materials used in a different element of the same component, e.g. a catch mechanism and the flexible arm on which it resides, or for example a return mechanism and the body which it acts upon (e.g. a spring and the actuator). In some aspects, the material which can be used to construct one or more components of the indicator apparatus include plastics, polymers, nylon, metals, or silicone materials. For example, potential construction materials can include styrenes or blends of styrenes and polymers. According to certain embodiments, materials which may be used to construct the components of the indicator apparatus include acrylonitrile butadiene styrene (ABS), polycarbonate/acrylonitrile butadiene styrene terpolymer blend (PC/ABS), polyoxymethylene (POM), nylon, stainless steel, polytetrafluoroethylene (PTFE), neoprene, and/or silicone rubber.

A benefit of some indicator devices described herein is the relatively low number of components and/or relatively small counter size that can be incorporated in the device. The small size of the indicator apparatus allows such devices to be, e.g., pocket-sized, or personal carrying item size, such as a size that is suitable for carrying in a purse or backpack.

According to some embodiments, the indicator apparatus is less than about 3 cm tall. E.g., an indicator device can be less than about 2.8 cm, less than about 2.6 cm, less than about 2.4 cm, less than about 2.2 cm, less than about 2 cm, less than about 1.8 cm, less than about 1.6 cm, less than about 1.4 cm, less than about 1.2 cm or less than about 1 cm in height. In an aspect, the height of the device is about 1-about 3 cm, such as about 1-2 cm (or 1 cm-about 2.5 cm).

According to embodiments, the indicator apparatus is also or alternatively less than about 3 cm wide. E.g., an indicator device can be less than about 2.8 cm, less than about 2.6 cm, less than about 2.4 cm, less than about 2.2 cm, less than about 2 cm, less than about 1.8 cm, less than about 1.6 cm, less than about 1.4 cm, less than about 1.2 cm, or less than about 1 cm in width. In one aspect, the device has a width of about 1-about 3 cm, such as about 1-about 2 cm.

According to some embodiments, the indicator apparatus is less than about 3 cm deep. E.g., an indicator device can be less than about 2.8 cm, less than about 2.6 cm, less than about 2.4 cm, less than about 2.2 cm, less than about 2 cm, less than about 1.8 cm, less than about 1.6 cm, less than about 1.4 cm, less than about 1.2 cm or less than about 1 cm in depth (e.g., about 1-2.5 cm).

According to some embodiments, the indicator apparatus occupies less than 5 cm$^3$ of total space, such as less than about 5 cm$^3$, less than about 5.5 cm$^3$, or less than about 4 cm$^3$ of total space. That is, according to some embodiments, the indicator apparatus occupies less than about 3.8 cm$^3$, less than about 3.6 cm$^3$, less than about 3.4 cm$^3$, less than about 3.2 cm$^3$, less than about 3 cm$^3$, less than about 2.8 cm$^3$, or even less, such as less than about 2.6 cm$^3$, less than about 2.4 cm$^3$, less than about 2.2 cm$^3$, or even less than about 2.0 cm$^3$ (e.g., about 2-about 4 cm$^3$).

As noted elsewhere, the event status indicator component/device of the invention can be associated with another device or system. In one exemplary aspect, the invention provides a treatment/medicine dispensing device (e.g., an energy applying treatment or a medicament dose dispenser) comprising an event-related indicator apparatus according to any embodiment described herein. According to some embodiments, the associated device is a material dispenser, such as a dose dispenser, such as a medicine dose dispenser. Such a dose/material dispenser can have a dispenser body which houses the event-related indicator apparatus and further comprises a substance/formulation dispensing element to facilitate the administration of the substance or formulation being dispensed by the dispenser and optionally further a dispensing element protective cover. The dose/material dispenser can also comprise an area for housing a container of material, e.g. medicine, to be dispensed. The dispenser body can comprise an optional indicator apparatus cover which can serve to provide access to the indicator apparatus within the dispenser body of the dispenser. The dispenser body can optionally further comprise a status identifier that works with the status indicators of the component/device of the invention to impart status information. In certain embodiments the status identifier is a viewing window, the viewing window optionally comprising a viewing window cover (in other aspects the status identifier can be a light, a line, an arrow, or the like, or any thereof, alone or in combination with a window or other means of focusing the attention of the user to the current indicators). In one exemplary aspect the medicine dispenser is a medical/pharmaceutical inhaler, such as a metered dose inhaler. A dispenser can comprise any suitable dispensing element, such as a mouthpiece or an element facilitating nasal administration, or an injector. According to certain embodiments, the dispensing element of the dose dispenser can have a protective cover as is common in the art (e.g., a dust cover, which may in some cases be removable).

As noted above, according to some embodiments the associated device/system used with the event indicator device/component can comprise a status identifier to identify which of the first set of indicators and which of the second set of indicators of the indicator apparatus housed therein reflects the current event status (e.g., a viewing window). A viewing window can be of sufficient size so as to facilitate the clear and unimpeded viewing of the visual message being displayed by the indicator apparatus housed therein, which typically will comprise a durable, often inert, and relatively clear or see-through material, such as a plastic, glass, or the like, which may be clear or colored.

According to embodiments, the present invention is a metered dose inhaler device incorporating an event-related indicator apparatus and having a dispenser body comprising a mouthpiece, a viewing window, and the dispenser body or housing being configured to house a pressurized aerosol medicine container. In some aspects, the dose dispenser of such a device or a similar medical device can serve to provide the actuation or event trigger for the indicator apparatus housed therein. As an example, the dose dispenser may be an inhaler of the type used in e.g. pharmaceutical broncho-therapeutic drug delivery, such as pressurized metered-dose inhalers (pMDIs) or dry powder inhalers (DPIs). The medicament dispenser can be an inhaler which can also or alternatively utilize a blister strip as a means of containing a medicament, wherein each blister of the strip contains a dose of powdered medicament. Other types of dispensers which may benefit from incorporating dose counting can be any kind of pre-filled container or tablet/capsule dispenser wherein there is no simple way for the user to visualize the amount of medicament remaining and available for administration. Any or all of the described medicament dispensers can be configured so as to comprise an indicator apparatus as described herein. In some aspects, a user can push, pull, squeeze, contract, trigger, or initiate other movements or actions to activate the dose dispensing device housing both the medicament to be administered and the indicator apparatus as a means of administering the medicament. Such a movement or action can, in some embodiments, also serve as an actuation trigger for the indicator apparatus.

In some embodiments, the components of the medicament dispenser and/or the event indicator component are all made of a single material. In alternative embodiments, one or more components can be made of different materials. In some aspects, one or more components of the medicament dispenser can comprise one or more materials. In some aspects, the material which can be used to construct the components of the medicament dispenser include plastics, polymers, nylon, metals, or silicone materials. For example, potential construction materials can include styrenes or blends of styrenes and polymers. According to certain embodiments, materials which can be used to construct the components of the medicament dispenser include acrylonitrile butadiene styrene (ABS), polycarbonate/acrylonitrile butadiene styrene terpolymer blend (PC/ABS), Polyoxymethylene (POM), nylon, stainless steel and/or silicone rubber.

Dose dispensers described herein are capable of housing medicament containers of many shapes and sizes, such as in bottles, canisters, strips, tablets and the like. The medicament containers can comprise a wide range of medicaments; such medicaments each comprising one or more active pharmaceutical ingredients (APIs) The one or more active pharmaceutical ingredient(s) (APIs) that can be dispensed from a dose dispenser comprising the indicator apparatus according to any aspects described herein can be selected from analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); anti-infectives e.g., cephalosporins, penicillins, streptomycin, sulfonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6a,9a-difluoro-1 ip-hydroxy-16a-methyl-3-oxo-17a.-propionyloxy-androsta-1,4-diene-17P-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline (epinephrine), fenoterol (e.g. as hydrobromide), formoterol (e.g. as fumarate), arformoterol, clenbuterol, olodaterol, indacaterol, isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or sibenadet, vilanterol, levoalbuterol, procaterol; adenosine 2a agonists, e.g. 2R,3R,4S,5R)-2-[6-Amino-2-(1 S-hydroxymethyl-2-phenyl-ethylamino)-purin-9-yl]-5-(2-ethyl-2H-tetrazol-5-yl)-tetrahydro-furan-3,4-diol (e.g. as maleate); a4 integrin inhibitors e.g. (2S)-3-[4-({[4-(aminocarbonyl)-1-piperidinyl]carbonyl}oxy)phenyl]-2-[((2S—)-4-methyl-2-{[2-(2 methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine, glycopyrronium (e.g. as bromide), aclidinium, umeclidinium or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

According to one embodiment, the indicator apparatus comprises at least two indicator wheels. In other aspects, the indicator apparatus comprises only two indicator wheels. The following description of the indicator apparatus in operation provides a description of such an embodiment having only two wheels. Multiple embodiments of the various elements of the device have been provided herein. It is the aim of this description to give the reader a full understanding of the operation of the indicator apparatus, specifically of the function and cooperative interaction of the components and elements of the indicator apparatus described herein. Such a description of one embodiment should not be interpreted as being either a) the sole embodiment in which the operation of the indicator apparatus can be successful or b) that the inventors have envisioned and described as their invention.

Principles of Operation

Although operation of the devices of the invention and components have been somewhat described above, the following disclosure of how devices of the invention can operate is also provided in order to better illuminate various aspects of the invention.

In use, an event trigger begins the actuation process, which causes the inventive device/component to operate, changing the position of one or more of the indicator components (e.g., the first wheel or both the first and second wheels) and thereby provide event status information to a user of the inventive component/device. Event triggers are described above.

Upon an event trigger (i.e., an actuation event), the energy from the event or trigger is received by an actuation means, such as an energy receiving member of an actuator, e.g. a boss or pin. In response to the receipt of energy from the event trigger the actuator moves, e.g. in a linear motion. The event trigger force received and transferred by the actuator actuates movement of components.

An actuator can transfer actuation energy from an event trigger to the first indicator member (e.g., a first wheel) via an energy transfer component/member, e.g. an actuator pawl. An actuator pawl, and in more specific embodiments an actuator pawl catch element, e.g., a ratchet tooth on an actuator pawl, engages with a corresponding part, e.g., a latching mechanism, e.g. first set of ratchet teeth, of or attached to the first wheel, so that energy (e.g., motion) of the actuator is transferred to, e.g., ratchet teeth of the first wheel, thereby causing the first wheel to rotate, thereby incrementing the first wheel via the first set of ratchet teeth on the first wheel one event increment.

In some embodiments the actuator means moves in a linear direction parallel to the axis of the substance container held within the dose dispensing device (e.g. medicament canister). In some embodiments the direction is linear to and/or offset from the longitudinal axis of rotation of the first and second wheel(s). In one embodiment the actuator moves in a linear direction offset from and perpendicular to the longitudinal axis of rotation around which the first and second wheels rotate.

According to the exemplary embodiment, during the incremental motion of the first wheel, the repositionable engagement unit responsible for driving the second wheel, e.g. the flex drive arm of the first wheel, naturally flexes inward unless forced otherwise, toward the longitudinal axis about which both the first and second wheels rotate. In this position, the first wheel flex drive arm may make contact with but does not engage with the second wheel latching mechanism, e.g. second set of teeth. The lack of engagement between the first wheel flex drive arm and the teeth on the second wheel does not result in any motion of the second wheel; that is, it results in rotational movement of the first wheel alone, while the second wheel remains stationary. According to the exemplary embodiment, during the incremental motion of the first wheel, the repositionable engagement unit responsible for stabilizing the second wheel, e.g. the flexible arm on the base, typically flexes inward unless forced otherwise, toward the longitudinal axis of rotation for both the first and second wheels. In such position, the wheel stabilizer element of the flexible arm on the base is engaged with the latching mechanism of the second wheel, e.g. second set of teeth, and stabilizes its position, preventing it from rotating with the first wheel.

In response to certain events, such as on occurrence of every occurrence of a set number of events, e.g. upon every tenth event trigger/actuation, which in some embodiments also or alternatively corresponds to a set number of rotations of the first wheel, the first wheel positioning element, e.g. first wheel deflector, comes into contact with the repositionable engagement unit responsible for stabilizing the second wheel, e.g. the base flexible arm and the base flexible arm deflector thereon. The first wheel deflector deflects the base flex arm via the flex arm deflector. As a result of the deflection of the base flex arm, the wheel stabilization element (e.g., pawl) of the base flex arm becomes disengaged from the second wheel, hence providing relief for the motion of the second/wheel; that is, freeing the second wheel to rotate along with the first wheel.

In an embodiment wherein the indicator apparatus comprises two wheels, one set number of events can determine the frequency with which a) the outer wheel is freed for rotation and b) the outer wheel is driven to rotate, each being accomplished by the mechanisms described herein. In an embodiment wherein the indicator apparatus comprises three or more wheels, one or more additional set number of events may dictate when each wheel beyond the first and second wheels rotate. Each set number of events can be different from one or more other set number of events. For example, according to an embodiment wherein the indicator apparatus comprises three wheels, the first wheel may rotate one increment upon every actuation/trigger event; the second wheel may rotate one increment upon every tenth actuation/trigger event; and the third wheel may rotate one increment upon every one hundredth actuation/trigger event.

According to certain embodiments, the deflection of the base flex arm as forced by the first wheel deflector, and the prevention of the deflection of the first wheel flex drive arm by interaction of the first wheel flex drive arm with the diversion element on the base, occurs intermittently but typically essentially synchronously or simultaneously, causing incremental motion of the second wheel. The spacing and arrangement of the indicator apparatus components and elements is such that this synchronicity is present. If such synchronicity is not present, the second wheel cannot rotate or cannot be rotated. That is, for example, if the second wheel is freed to rotate by the release of the wheel stabilizing element on the base flex arm, but the catch mechanism of the first wheel flexible drive arm is not positioned to drive the rotation of the second wheel, the second wheel will not rotate. Also or alternatively, if the catch mechanism of the first wheel flexible drive arm is in engaged with the latch mechanism of the second/outer wheel, but the wheel stabilizing element of the base flexible arm remains engaged with the second wheel latch mechanism, then the second wheel will not be free to rotate. According to one embodiment, such synchronous and simultaneous engagement and/or movement occurs upon every $10^{th}$ actuation of the driver/actuator. According to one embodiment, this synchronous and simultaneous engagement and/or movement occurs upon every $10^{th}$ actuation of the driver/actuator unless and until indicator apparatus has reached the end of its life cycle.

"Synchronously", "simultaneously" as used herein is intended to describe two actions that happen together at about the same time, such as within no more than about 2 seconds from each other, as in they occur no more than about 1.5 seconds from each other, as in completing the two actions within about 1 second of one another or less, such as the two steps being completed within about 0.5 seconds, about 0.25 seconds, about 0.20 seconds, about 0.15 seconds, or about 0.1 seconds or less from one another, such as within about 0.05 seconds, about 0.025 seconds, about 0.01 seconds of one another or even less, such as within less than about 0.005 seconds or within about 0.001 seconds of one another or less, such as at the same time as one another.

At the same time or substantially simultaneously that the second wheel is freed to rotate, the first wheel flex drive arm typically encounters the positioning element on the base, e.g., a stud on the base. Upon contact, a base stud prevents the natural disengagement of the repositionable engagement unit responsible for driving the second wheel, e.g. it prevents the flexion of the first wheel flex drive arm naturally occurring in a direction away from the latching mechanism of the second wheel, instead forcing the first wheel flex drive arm outward, toward the latching mechanism of the second wheel. This forced repositioning forces the catch mechanism on the first wheel flex drive arm to engage with the second wheel latching mechanism. This engagement forces the two wheels to rotate together, as the two wheels are engaged with one another, and the rotational motion of the first wheel is shared with or corresponds to the rotational movement of the second wheel, resulting in a single incremental rotation of the both the first and second wheels while the second wheel is substantially simultaneously freed for movement.

Upon each rotation of the first wheel and upon the shared rotation of the both the first and second wheels, the event indicator visual messaging display, e.g. the digits or indicia on the first wheel and/or the second wheel, can together display the event status, e.g. an event count, on the indicator apparatus as clarified by a status identifier on the indicator apparatus, e.g. an arrow, or via a status identifier such as a window in the body of a larger device housing the indicator apparatus.

After actuation, the event trigger is released, is complete, or is no longer active, allowing the actuator to return to its starting position via an element which returns the actuator to a start position after each actuation has occurred, such as a spring. In doing so, the catch, e.g. ratchet tooth on the energy transfer member of the actuator, e.g. actuator pawl, is capable of sliding over the latching mechanism, e.g. ratchet teeth, of the first wheel without further rotating the first wheel. At the same time the second wheel is maintained or held in position by the engagement with the repositionable engagement arm responsible for stabilizing the second wheel, e.g. the base flex arm.

According to embodiments, an indicator device does not reset to an initial event registration setting, for example start count, at the end of its life cycle, e.g., the device does not reset once it has counted up to a maximum intended count or down to a minimum count. According to alternative embodiments, the indicator apparatus can be reset to an initial event status by certain individuals having knowledge of, and access to means for, resetting the indicator apparatus. In some aspects, such individuals are physicians or device manufacturers.

The indicator apparatus can be designed to register an event occurrent upon a certain type or standard of actuation of the actuation means/actuator; that is, means can be incorporated so that an event is not registered unless the actuator means is actuated to a particularly sufficient standard. For example, in one aspect the first wheel (or first and second, or first, second and third or any further wheels comprised in the indicator apparatus) will not be driven to rotate one increment unless the actuation means (actuator) receives a sufficient amount of energy from the event trigger; e.g., in the case of a pump actuator the actuator is fully depressed and the energy transfer member, e.g. the actuator pawl, and its component catch mechanism have the opportunity to fully transfer energy to the first wheel latching mechanism so as to rotate it. That is, for example, if only a partial actuation trigger is experienced, the actuator will only receive a partial actuation force/energy and may only be partially actuated/activated; e.g., may only be partly depressed. Accordingly, the actuator pawl and its catch mechanism engaged with the first wheel latching mechanism will only start to rotate the first wheel one increment; but if the actuation is incomplete or insufficient, and the first wheel rotation does not reach a point where the actuator pawl catch mechanism ultimately disengages and slides over the adjacent tooth of the first wheel latching mechanism, upon the return motion of the actuator to a start position, the actuator pawl fixed tooth and the actuator itself will simply return to its start position without engagement with the first wheel, and the first wheel therefore also returns to its original position, not having registered a count, e.g. without having had the first wheel or the first and second indicator wheel advance/rotate.

In some embodiments, the location within the actuation stroke sufficient to trigger a rotation of the first wheel is such that the position is reached substantially simultaneously with, or essentially at the same time as, the release of substance (e.g. medicament or chemical) being dispensed by the dispensing device housing the indicator apparatus. In some embodiments, the location within the actuation stroke sufficient to trigger a rotation of the first wheel one increment is such that the location is reached just before the release or administration of the substance. In this manner, in a larger dispensing device, such as a medicament dispenser, if there is any bias to the registration of an event occurrence, it is toward the inclusion of an event which has not occurred versus toward the non-registration of an event which has occurred. In other words, count registration can favor over counting as opposed to under counting. While all attempts are made in design and manufacturing to make event registration as true and accurate as possible, that is, as synchronized as possible with the dispensation of medicament, in embodiments wherein the indicator apparatus is housed within a medicament dispenser, if there is any bias or "favoring" in a remaining dose count, it will be toward the location reached during an actuation stroke sufficient to trigger a rotation of the first wheel being reached just before the release or administration of the substance if the trigger cannot occur substantially simultaneously with or at essentially the same time as the dispensation or release of the substance. Accordingly, the patient can be alerted that there is less medicament available than is actually available. This is a common safety feature in such devices as it is safer for a user to have medicament available when the user believes they may not have such medicament available, than to believe they do have medicament available when needed and in fact the dispenser is empty.

Several features of the indicator apparatus can support or combine together with one another or with other components of an associated device/system and/or the event indicator component/device to support the accuracy, reliability, or durability of the event indicator apparatus itself or a larger device or system in which it is housed, and thereby impact related qualities such as safety when the associated device is a medicine/treatment dispensing device. One such optionally included feature is a lock out feature/component. For example, in connection with a treatment/medicament dispensing device when the treatments or medicine (e.g., full doses) have been exhausted, the substance storage container (e.g. medicament container or canister) is empty, and/or the indicator(s) indicate(s) that no doses remain, the actuator can, in certain embodiments, be held in a dispensed (fully depressed) position and/or not be permitted to return to a starting position, such that it cannot be actuated a further time. In another aspect, the actuator may return to a starting position, but it is restricted from being able to be actuated again by the configuration of one or more components of the system (e.g., a wheel or an element of a wheel, e.g. the second wheel, can engage the actuator, directly or indirectly, thereby causing a lock out of further use of the associated device). In another aspect, the actuator can be permitted to return to a starting position after a final dose administration, an element capable of visually blocking the visual event indicators (e.g. second wheel shutter) typically having moved into position upon the final dose administration to indicate device exhaustion (e.g. no doses of material held within remain), and the actuator can be "free" (in position or otherwise ready) to accept subsequent actuations, rotating the inner wheel upon each actuation, while the second wheel shutter typically remains in position over the event indicators indicating that no doses remain available. According to such an embodiment, the second wheel shutter can allow up to a set number of actuations and incremental advancements of the first wheel after moving into position, typically blocking the event indicators and indicating that no doses remain. Upon reaching a set number of actuations, e.g. ten actuations, after having moved into position blocking the event indicators, the actuation means/actuator can become locked, as the first wheel can be prevented from rotating the second wheel by the second wheel having become locked at the shutter position. According to certain embodiments, the actuator can be held in a dispensed (fully depressed) position, not returning to a starting position, after being actuated for a final time by means present to interrupt the return motion of the actuator. The lock-out feature can, therefore, when incorporated in a dispensing device, prevent the dispensing of an incomplete dose of substance, e.g. medicament, as it prevents the actuation of the actuator if the indicator apparatus has counted down to, or up to, the point of its exhaustion. According to one embodiment, a lock-out feature is not incorporated into the device/component or associated device/system.

An additional inherent safety feature of the indicator apparatus in certain aspects is the mechanical cooperation of the elements of the first wheel, second wheel, and base such that it takes a full actuation in order to advance the necessary wheels (e.g. first or first and second wheels) of the indicator apparatus and hence to register an event count. For example, in one aspect the first wheel (or first and second wheels) will not be driven to rotate one increment unless the driver is fully depressed and the driver pawl and its component fixed ratchet tooth have the opportunity to fully transfer energy to the set of ratchet teeth on the first wheel so as to rotate it sufficiently such that upon release, the actuator pawl slides over a neighboring ratchet tooth on the first wheel versus simply allowing the first wheel to rotate back to its original position while the driver returns to its original, starting position. That is, for example, if only a partial actuation trigger is experienced, the actuator will only be partially depressed. Accordingly, the actuator pawl and its attached fixed ratchet tooth engaged with the ratchet teeth of the first wheel will only start to rotate the first wheel one increment; but if the actuation is incomplete, and the first wheel rotation does not reach a point, e.g. a location within the actuation stroke, where the actuator pawl ultimately disengages and slides over the adjacent ratchet tooth of the first wheel, upon the return motion of the actuation means to a start position, the fixed ratchet tooth on the actuator pawl and the actuator will simply return to its start position without engagement with the first wheel, and the first wheel therefore also returns to its original position, not having registered a count, e.g. without having had the first wheel or the first and second wheel advance a single increment in rotation. In order for the first wheel to rotate, the actuator must impart a large enough force, and over a long enough distance, that the actuator pawl pushes on a ratchet tooth of the first wheel sufficiently so as to rotate it far enough so that when the actuation force is released, the actuation pawl (ratchet tooth of the actuation pawl) slides over the neighboring first wheel ratchet tooth versus simply allowing the first wheel ratchet tooth to follow the actuator (e.g. the ratchet tooth on the actuator pawl) back to its starting position, e.g. the first wheel counter-rotating slightly (e.g. by the amount initially rotated in a first direction by the partial actuation) back to its start position. Meanwhile, unless it is upon a set number of events, e.g. the $10^{th}$ event, or also referred to as an intermittent, actuation wherein the base flex arm has disengaged from the second wheel, the second wheel is held in place and will not rotate; in the case of a partial $10^{th}$ actuation, the base flex arm will not disengage from the second wheel sufficiently so as to release it; hence when the partial actuation is released and the actuation means returns to its original position, so will the second wheel, and no additional count will be registered.

Description of Exemplary Embodiments with Reference to the Figures

Without being restricted to any single design, to aid in understanding of the invention presented herein, a detailed description of an exemplary embodiment of the invention is provided and described with the Figures disclosed herewith, to better illustrate how the devices of the invention are configured and operate.

In this exemplary embodiment, an indicator apparatus having the following components and elements is presented: (a) an actuator that is in the form of a plunger; and that comprises an actuator pawl, which actuator pawl in turn comprises a fixed ratchet tooth-style catch; (b) two event indicator wheels (a first (inner) wheel and a second (outer) wheel), each comprising a latching mechanism in the form of respective sets of teeth, the first wheel set of teeth embodied as ratchet teeth, and each wheel comprising a set of event indicators in the form of sets of numeric digits; (c) two repositionable engagement units in the form of (i) a flex drive arm attached to the first wheel to drive rotation of the second wheel, further comprising a catch to engage with the second wheel latching mechanism embodied as a set of teeth, and (ii) a flex arm attached to the base to stabilize the second wheel and further comprising a catch in the form of a pawl and a deflector; and (d) two positioning elements, one embodied as a deflector on the first wheel and the second embodied as a stud on the housing. The exemplary event indicator component is presented as part of an MDI.

FIG. 1 shows the MDI 21 comprising a dispenser body 24 and an event-related indicator (dose counting) apparatus 1. The dispenser body 24 comprises a status identifier embodied as a window 20, an optional indicator apparatus cover 23 which can serve to provide access to the indicator apparatus within the dispenser body of the dispenser, and a dispensing means (e.g. mouthpiece) cover or dust cap 25. The dispenser body houses a canister (not shown) containing a medicament to be dispensed. In this embodiment the indicator apparatus 1 is located at the bottom of the metered dose inhaler 21 as shown in FIG. 1.

Figure 2:
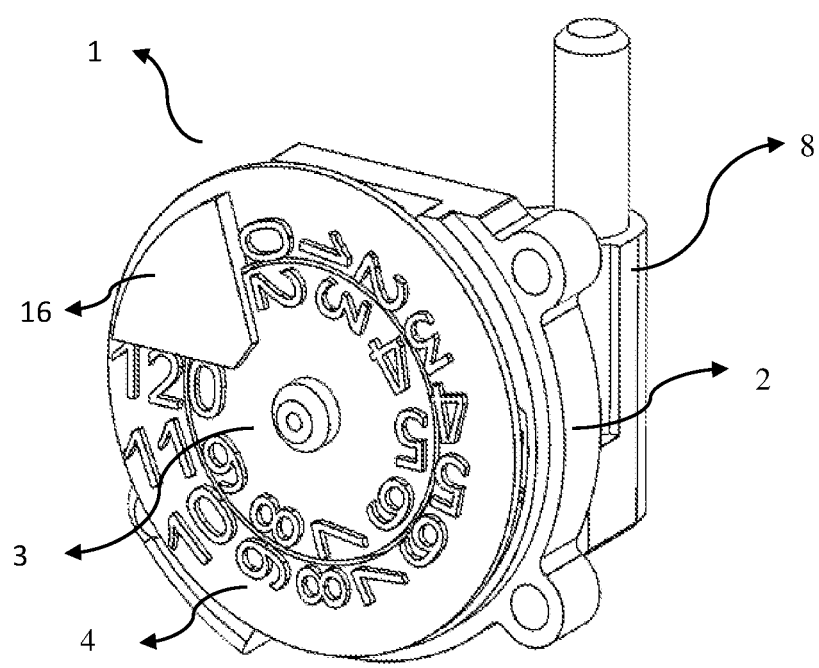
FIG. 2 shows an isometric view of an embodiment of the event-related status indicator apparatus.

FIG. 2 shows an isometric view of the exemplary indicator apparatus/dose counter 1. The indicator apparatus/dose counter comprises a first wheel 3, a second wheel 4, a base 2, and an actuator that is in the form of a plunger 8. The first wheel 3 is located in the base 2 with the help of a central boss 15 of the first wheel (see also FIG. 9).

The second wheel 4 is assembled coaxially around a part of (the part of the inner wheel comprising indicator elements), and over a part (the outer rim) of the first wheel 3 such that the front face of both the wheels are co-planer. The first wheel 3 and the second wheel 4 co-operate with each other to define a common display and/or event indicator zone that is visible in an event identifier, e.g. viewing window 20.

Figure 3:
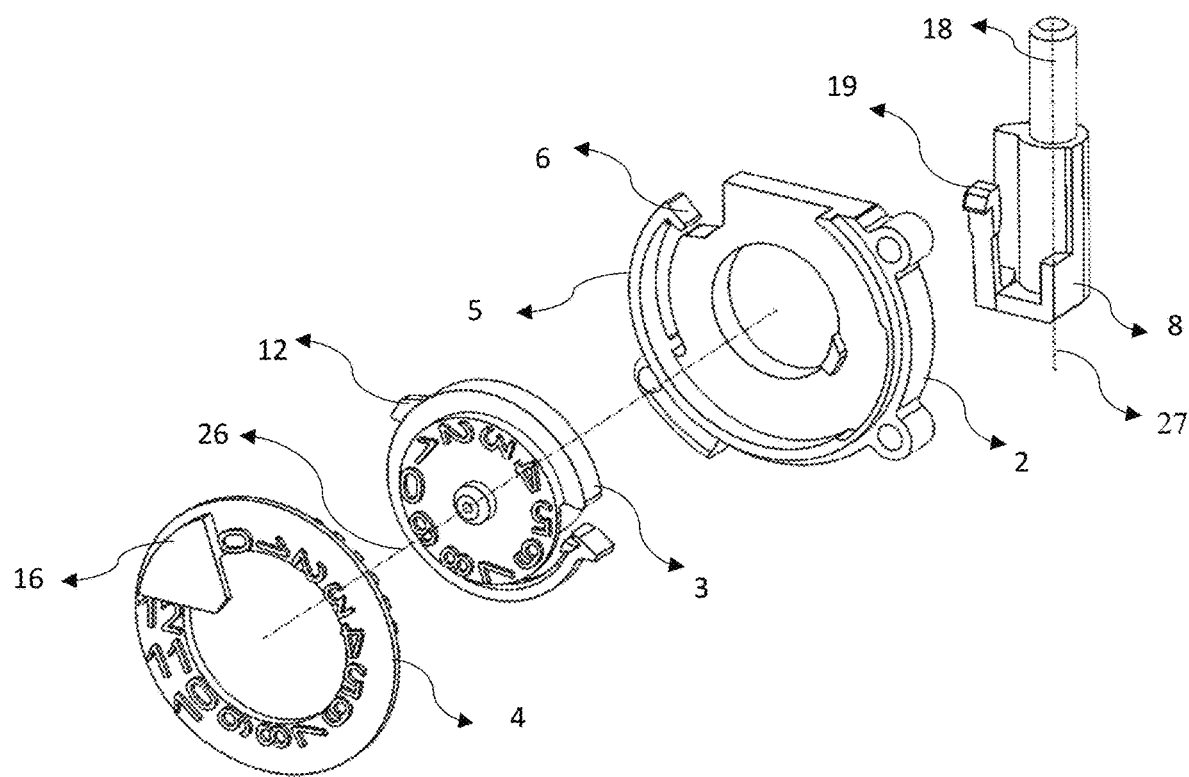
FIG. 3 shows an exploded view of an embodiment of the event-related status indicator apparatus.

FIG. 3 provides exploded view of several components of the indicator apparatus/dose counter, including the first wheel 3, the second wheel 4, the base 2 and the actuator (plunger) 8. The first wheel 3 and the second wheel 4 are mounted on the base 2. The base 2 defines the longitudinal axis 26 of rotation. First wheel 3 and second wheel 4 rotate about the shared longitudinal axis 26 of rotation. The actuator, or plunger, 8 moves in a linear direction along the axis 27 which is offset to the longitudinal axis 26 in response to the motion of the canister (not shown) or medicament dispenser during actuation.

Figure 4A:
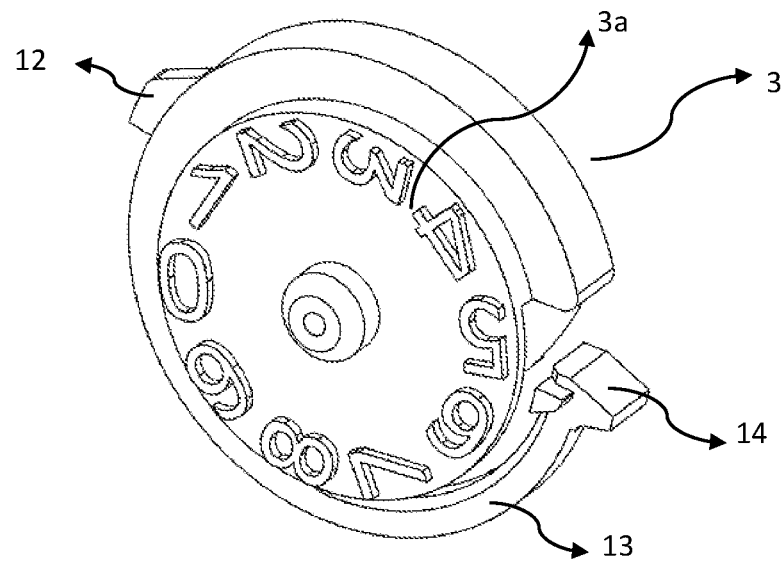
FIG. 4a shows a front side isometric view of an embodiment of the first (inner) wheel of the event-related status indicator apparatus.
Figure 4B:
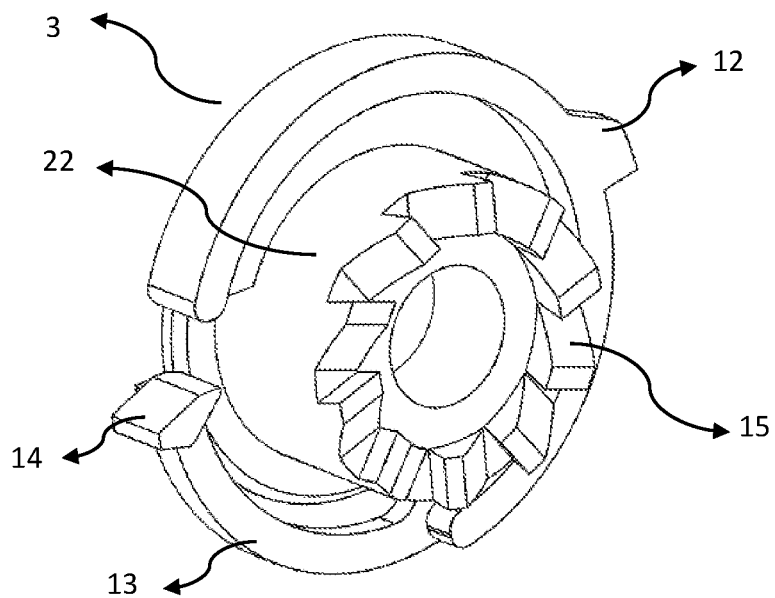
FIG. 4b shows a back side isometric view of an embodiment of the first (inner) wheel of the event-related status indicator apparatus.

FIG. 4a shows a front view of first wheel 3 and FIG. 4b shows the rear view of first wheel 3. The first wheel 3 comprises a repositionable engagement unit embodied as a flex drive arm 13, a catch on the repositionable engagement unit embodied as a second wheel driver tooth 14, a positioning element embodied as a deflector 12, a central boss 22 and a latching mechanism embodied as a first set of teeth 15 which in the illustrated embodiment are ratchet teeth. The front face 3a of the first wheel is printed, imprinted, carved, etched, pasted, scored, burned, or embossed to show the one or more series event indicators, embodied as the numerals "0" to "9". In FIG. 4a, the front face 3a of the first wheel 3 has the series of numbers from "0" to "9" printed, imprinted, carved, etched, pasted, scored, burned or embossed thereon. The first set of ratchet teeth 15 are arranged circumferentially over the central boss 22 of the first wheel 3. The first wheel 3 is mounted on the base 2 with the help of central boss 22. The first wheel 3, or at a minimum the face or plane of the first wheel comprising the event indicators, has a diameter less than the second wheel 4. The second wheel 4 is assembled over the first wheel 3 in an overlapping configuration such that the front face of both the wheels are co planer and form a common display and/or counter zone (refer to FIG. 2). The first wheel 3 is driven by the energy transfer member of the actuator, embodied by an actuator pawl 19 on the actuator 8 via the first set of ratchet teeth 15. Flex drive arm 13 is a part of (e.g. integral to) the main body of the first wheel 3. The flex drive arm 13 of the first wheel 3 comprises a second wheel driver tooth 14. The second wheel driver tooth 14 is in contact with the second wheel latching mechanism, embodied as a second set of teeth 17 of the second wheel 4. The second wheel driver tooth 14 and second set of teeth 17 are disengaged during movement of the first wheel 3 until flex drive arm 13 of the first wheel 3 engages with a positioning element, embodied as a stud 9 on the base 2. When the flex drive arm 13 of the first wheel 3 engages with stud 9 (refer to FIG. 6a) on the base 2, the flex drive arm 13 is unable to flex inwards or towards the longitudinal axis and as a result of this the second wheel driver tooth 14 is pushed outward to engage with the second set of teeth 17 and drives the second wheel 4 via second set of teeth 17 causing the second wheel 4 to rotate. At the same time, a positioning element on the first wheel, embodied as deflector 12 on the first wheel 3 deflects the flex arm 5 via corresponding deflector 7 on the base 2 and releases the second wheel 4 from the catch, embodied as a pawl 6 on the base flex arm 5. Pawl 6 prevents the reverse rotation of the second wheel 4. The teeth 17 on the second wheel 4 and their engagement with the second wheel driver tooth 14 prevent the reverse rotation of the first wheel 3. Reverse rotation of the first wheel 3 is also prevented by the ratchet design of elements of the actuator 8 (specifically the shape of the actuator pawl 19) and the first wheel first set of teeth 15.

Figure 5A:
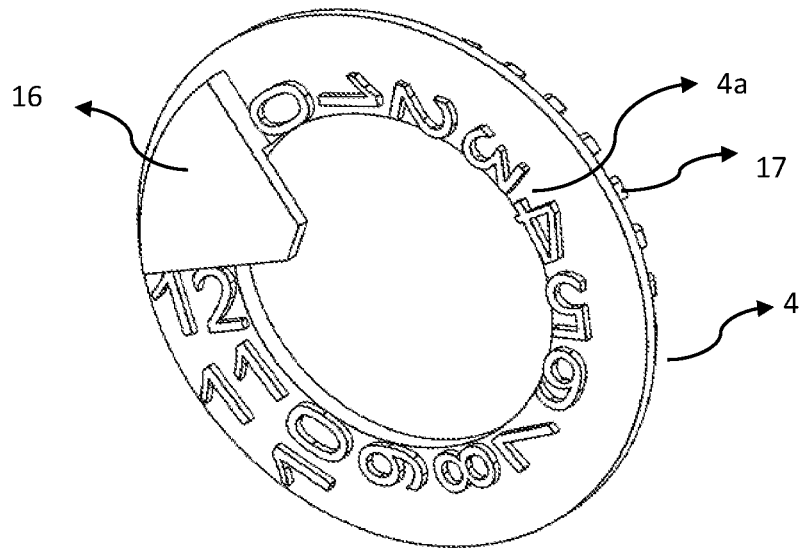
FIG. 5a shows a front side isometric view of an embodiment of the second (outer) wheel of the event-related status indicator apparatus.
Figure 5B:
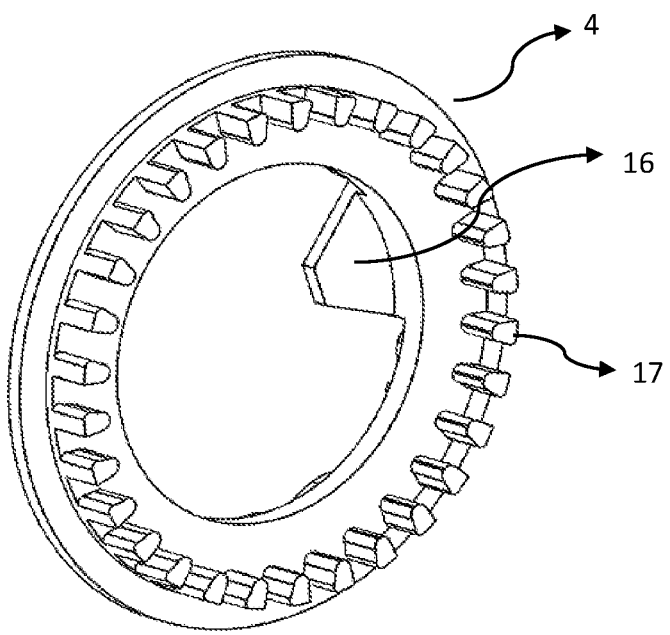
FIG. 5b shows a back side isometric view of an embodiment of the second (outer) wheel of the event-related status indicator apparatus.

FIG. 5a shows a front view of second wheel 4 and FIG. 5b shows the rear view of the second wheel 4. The second wheel 4 comprises an element for blocking the visual display of event indicators, embodied as a shutter 16 and second set of teeth 17. The front face 4a of the second wheel 4 is printed, imprinted, carved, etched, pasted, scored, burned or embossed to show one or more series of the numbers from "0" to "12". The shutter 16 is provided on the second wheel 4 to indicate the end of life of the product, e.g. no doses are left. At the end of life of the product or when no doses remain, the shutter 16 occupies or closes off the window indicating exhaustion of the dispenser. Second wheel 4 is driven by driver tooth 14 attached to the flex drive arm 13 of the first wheel 3. The driver tooth 14 is in contact with the second set of teeth 17 on the second wheel 4. The reverse rotation of the second wheel 4 is prevented by pawl 6 on the base 2. Second set of teeth 17 along with the second wheel driver tooth 14 are also responsible for prevention of reverse rotation of the first wheel 3. Second wheel 4 increments after every set number of events or actuation of the actuator 8, e.g. upon every 10 events, or one complete rotation of the first wheel 3.

Figure 6A:
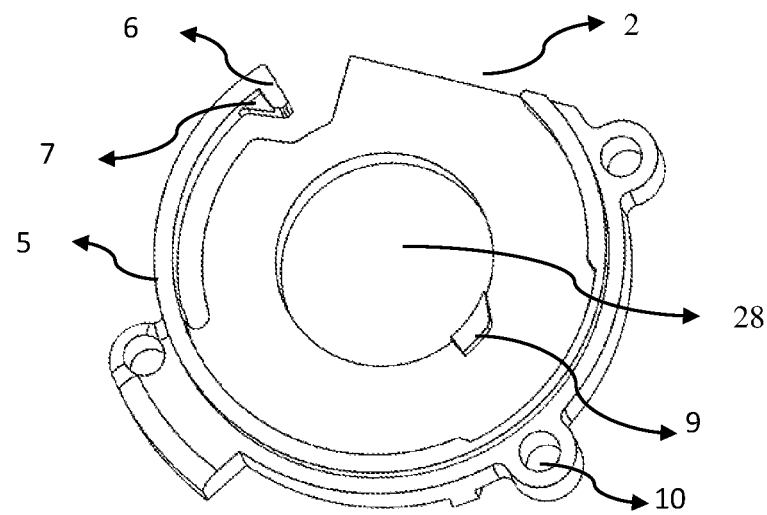
FIGS. 6a and 6b show different isometric views of embodiments of the base of the event-related status indicator apparatus.
Figure 6B:
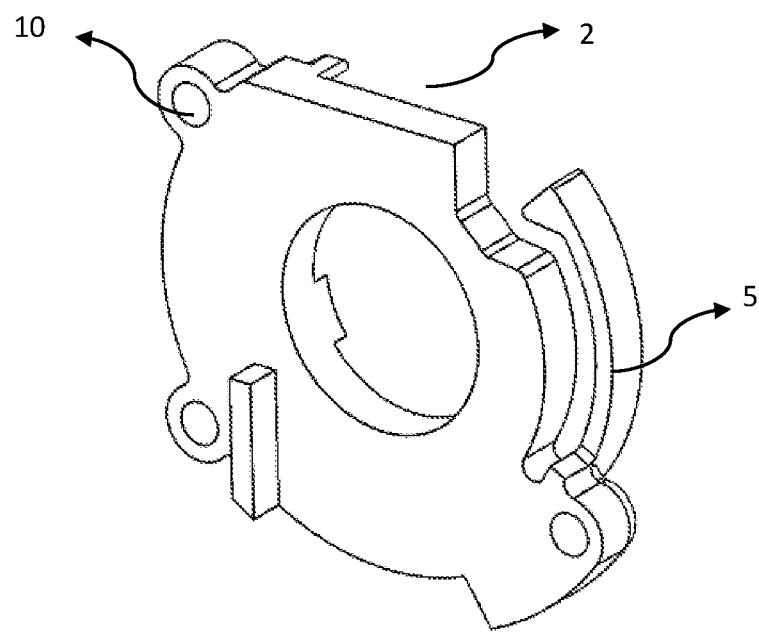

FIGS. 6a and 6b show different isometric views of an embodiment of the base 2 of the exemplary indicator apparatus/dose counter 1. The base 2 acts to house some or all of the other elements of the indicator apparatus 1. The base supports the first wheel 3 and the second wheel 4. The base 2 also comprises one or more fastening or attachment mechanisms, embodied as mounting holes 10 to mount the base to the body of the medical device 21. The base 2 comprises a central bore 28 to mount or locate the first wheel 3 and/or the second wheel 4. The base 2 functions to mount and locate the first wheel 3 and the second wheel 4 relative to one another while allowing both wheels to rotate about the longitudinal axis 26. The base 2 comprises a repositionable engagement unit to stabilize the second wheel, embodied as a flex arm 5 having a catch, embodied as a pawl 6 and the deflector 7 integral to the flex arm. The pawl 6 on the flex arm 5 of the base 2 prevents the reverse rotation of the second wheel 4. Flex arm 5 does not flex or deflect until the deflector 12 on the first wheel 3 comes into contact with the deflector 7 on flex arm 5 of the base 2. The flex arm 5 on the base 2 is intermittently deflected by the deflector 12 on the first wheel outward and away from the longitudinal axis 26 (see also FIG. 3). After a set number of events, for example every ten actuations of the actuator 8, deflector 12 of the first wheel pushes or deflects the flex arm 5 of the base 2 via the deflector 7 on the flex arm 5. The deflection of the flex arm 5 frees the second wheel 4 for incremental movement, allowing its rotation with the first wheel.

As shown in FIGS. 6a and 6b, the base 2 also comprises the positioning element embodied as stud 9. The stud 9 on the base 2 prevents the natural flexion of the flex drive arm 13 of the first wheel 3, forcing a new position of the flex drive arm 13, thereby forcing the second wheel driver teeth 14 of the flex drive arm 13 of the first wheel 3 to engage with the second wheel second set of teeth 17 and thereby resulting in the incremental movement of the second wheel 4 about the axis of rotation. The flex drive arm 13 of the first wheel 3 flexes inwardly towards longitudinal axis 26 during every actuation of the actuator 8 unless it comes into contact with the stud 9 of the base 2. After every ten actuations of the actuator 8, the flex drive arm 13 on first wheel 3 comes into contact with the stud 9 of the base 2 allowing the incremental movement of the second wheel 4 via engagement of the second wheel driver tooth 14 and second set of teeth 17. The deflection of the flex arm 5 of the base 2 and the prevention of the flexion of the flex drive arm 13 on the first wheel 3 occurs intermittently but substantially simultaneously to allow the incremental motion of the second wheel 4. This particular arrangement ensures the free release of the second wheel 4 from the pawl 6 to allow the second wheel driver teeth 14 of the flex drive arm 13 to increment the second wheel 4. The base can position the first wheel 3 and the second wheel 4 in the place by snap-fit or push fit assembly or mechanism (not shown).

Figure 7:
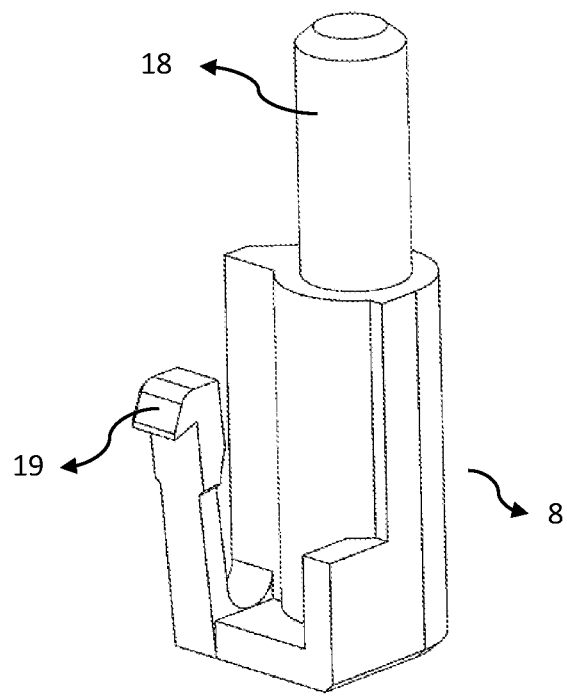
FIG. 7 shows an isometric view of an embodiment of an actuator of the event-related status indicator apparatus.

FIG. 7 shows an isometric view of the actuator 8. The actuator comprises an energy transfer member, embodied as an actuator pawl 19, and an energy receiving member, embodied as a circular boss 18. The actuator 8 moves in a linear direction along the axis offset axis 27 in response to the motion of the canister or medicament dispenser during actuation. In this embodiment, the circular boss 18 is in contact with the canister during actuation (not shown). Movement of Pawl 19 engages with and drives the first set of the ratchet teeth 15 on the first wheel 3, causing rotation of the first wheel 3. The actuator 8 is spring loaded with the spring located on the surface opposite to the circular boss 18 (not shown). The spring assists the actuator 8 to return the actuator to its original position or non-dispensing position after actuation/operation.

FIGS. 8-12 show an illustration of the working of the indicator apparatus, embodied as a MDI dose counter, 1 with an initial dose count of '120' number of doses. The digits on the second wheel 4 and the first wheel 3 together display the dose count through the status identifier window 20. In this example, the medicament dispenser starts with 120 available doses, and the indicator apparatus is designed to count down the number of remaining doses available after each actuation.

Figure 8:
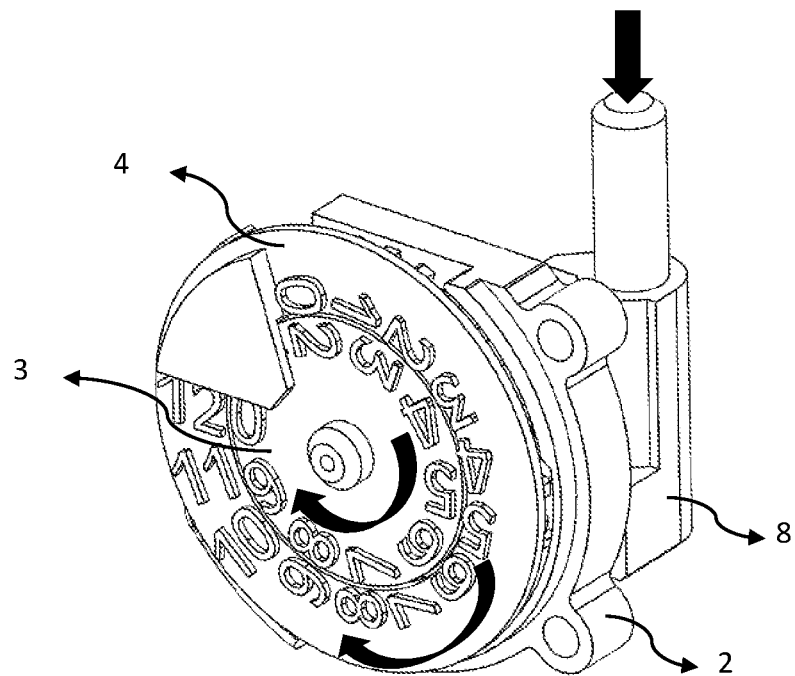
FIG. 8 shows an operating cycle of an embodiment of the event-related status indicator apparatus at the beginning of an event registration.
Figure 9:
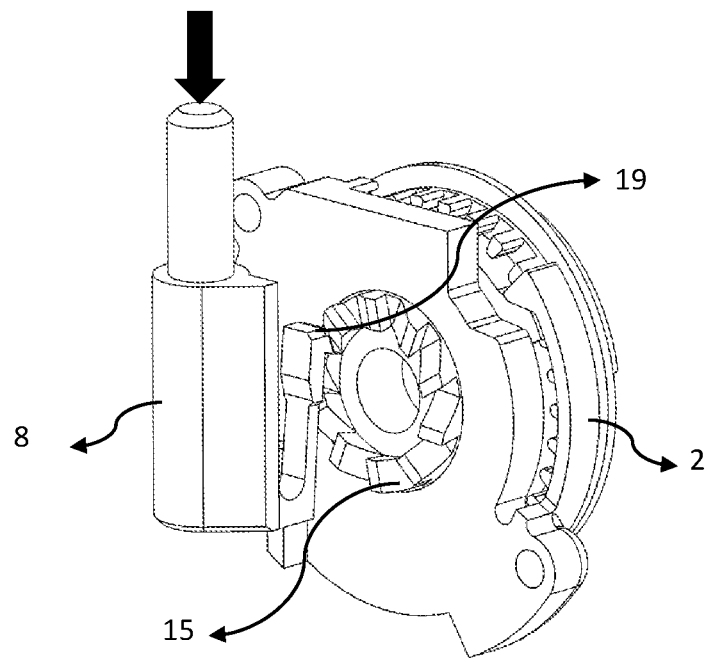
FIG. 9 shows a back-side view of an embodiment of the event-related status indicator apparatus shown in FIG. 8.

FIG. 8 and FIG. 9 show the operating cycle of the indicator apparatus 1 at the beginning of the actuation. During operation of the medicament dispenser or device in which the indicator apparatus is housed, an event trigger occurs. For example, the event trigger can be that the medicament container (e.g. medicament canister) is depressed either by the press- and breathe operation of the user or the activation of a breath triggered actuation mechanism, both resulting in downward liner motion of the canister. This results in downward liner movement of the actuator 8, as the energy receiving member receives the energy from the actuation trigger. In the present FIGS. 8 and 9, as the actuator 8 begins moving downward, the dose count begins decreasing from '120' to '119'.

The energy transfer member, e.g. actuator pawl 19 on actuator 8 which is in contact with the first set of ratchet teeth 15 of the first wheel 3 moves linearly in response to the movement of the medicament canister thereby incrementing (decrementing or decreasing the number) the first wheel 3 via the first set of ratchet teeth 15 (refer FIG. 9). At this stage, the indicator apparatus 1 begins by reading '120' thereby displaying '0' on first wheel 3, and '12' on second wheel 4. When the canister is depressed to actuate/operate the medicament dispenser (not shown), the motion is received by and transferred from the actuator 8. The actuator pawl 19 on the actuator 8 engages and starts rotating the first wheel 3 via first set of ratchet teeth 15. At this stage the first wheel 3 starts decrementing or decreasing from '0' to '9', as this actuation is occurring upon a set number of events, e.g. the 10$^{th}$ event. During this time, incremental motion of the first wheel 3 also results in the incremental motion of the second wheel 4 in the same direction. When the first wheel 3 starts decrementing from '0' to '9', the second wheel 4 starts decrementing the '12' to '11'.

Figure 10:
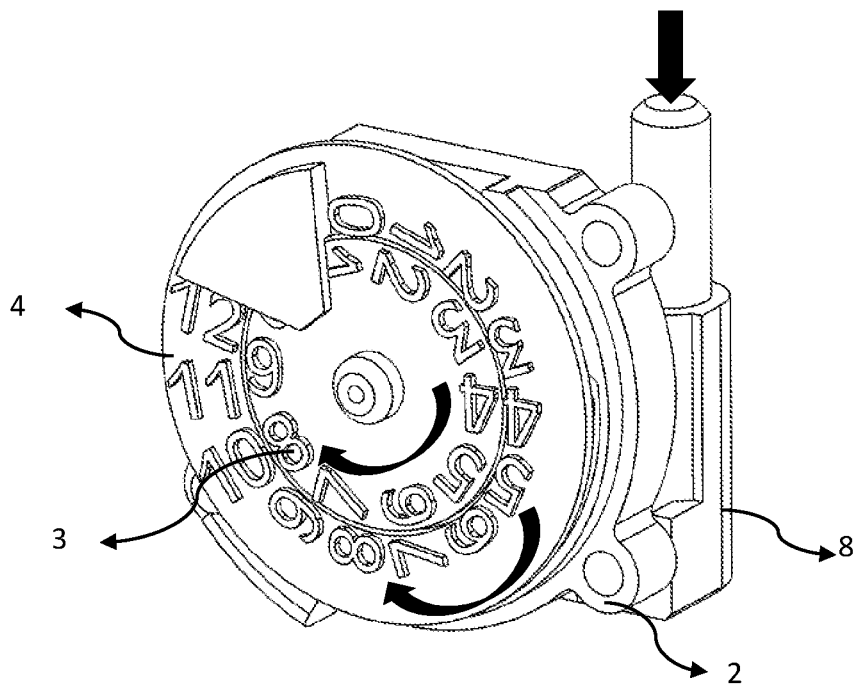
FIG. 10 shows an operating cycle of an embodiment of the event-related status indicator apparatus in the middle of an event registration.
Figure 11:
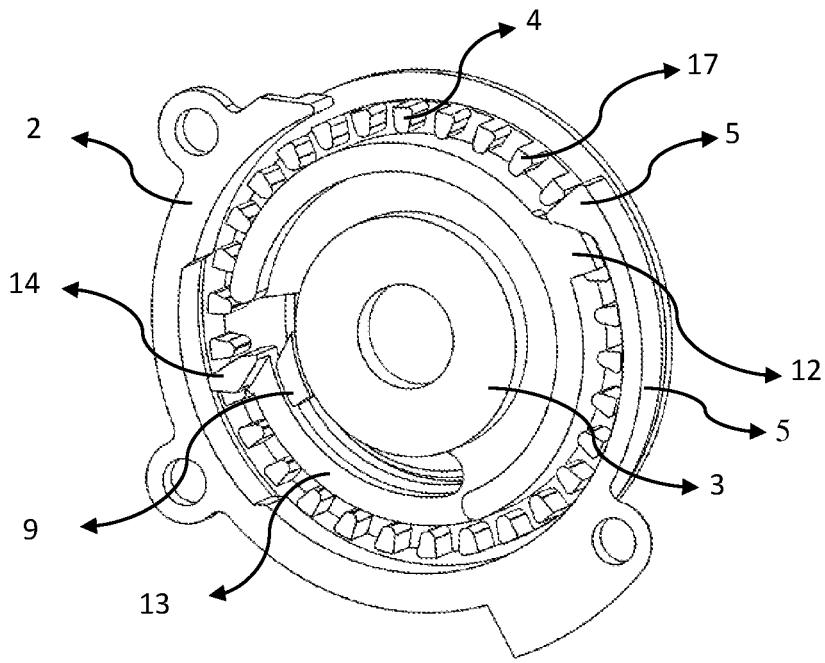
FIG. 11 shows a sectional view of an embodiment of the event-related status indicator apparatus shown in FIG. 10.

FIG. 10 shows the operating cycle of the indicator apparatus 1 in the middle of the actuation and FIG. 11 shows the sectional view of the indicator apparatus showing the mechanism of operation for the rotation of the second wheel 4 via the catch on the repositionable engagement unit, e.g. flex drive arm on the first wheel, embodied as the second wheel driver tooth 14. The actuator 8 continues to move linearly downward in response to the movement of the medicament canister thereby incrementing the first wheel 3 and the second wheel 4. As the first wheel rotates, the positioning unit, e.g. deflector, 12 on the first wheel 3 relieves the second wheel 4 by deflecting the catch, e.g. pawl 6 on the base flex arm 5 via corresponding deflector 7. At the same time, the flex drive arm 13 on the first wheel 3 comes into contact with stationary positioning element, e.g. stud 9 on the base 2. This prevents the flexion of the flex drive arm 13 on the first wheel 3 and forces the second wheel driver tooth 14 to increment the second wheel 4 via the latching mechanism on the second wheel, e.g. second set of teeth 17. Both the first wheel 3 and the second wheel 4 continue to rotate in the same direction. The operation referred in FIG. 10 or FIG. 11 occurs after every ten actuations of the actuator 8. After every ten actuations of the actuator 8, the flex drive arm 13 on first wheel 3 comes in contact with the stud 9 of the base 2 allowing the incremental movement of the second wheel 4 via engagement of the second wheel driver tooth 14 and second set of teeth 17. The reverse rotation of the first wheel is prevented by the gear teeth 17 on the second wheel 4 and the second wheel driver tooth 14. The reverse rotation of the first wheel is also prevented by the ratchet mechanism defining the engagement between the actuator 8 and the first wheel first set of teeth 15 as previously described.

Figure 12:
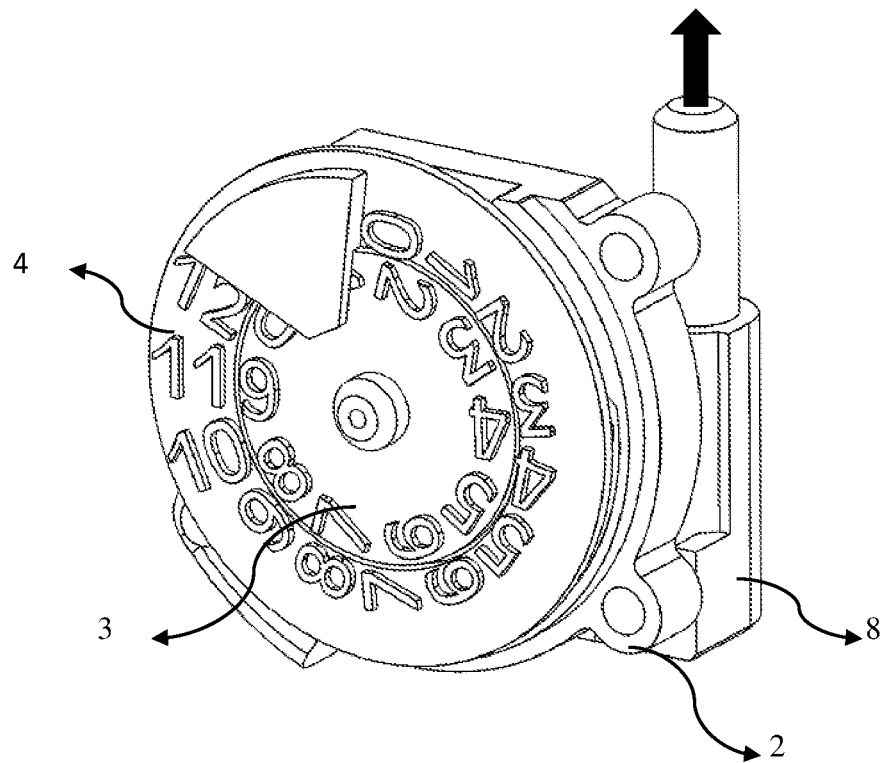
FIG. 12 shows an operating cycle of an embodiment of the event-related status indicator apparatus at the end of an event registration.

FIG. 12 shows the operating cycle of the indicator apparatus 1 at end of an actuation and return of the actuator 8 to its original position due to a spring (not shown). At this stage the canister is fully depressed and/or the dose is fully dispensed and now the canister returning to its original or non-dispensing position. At the end of the actuation the actuator 8 completes the linear stroke in response to the movement of the canister. Both the first wheel 3 and the second wheel 4 complete their respective incremental motion. At this stage, the dose count moves down one unit to displays '119' thereby displaying '9' on first wheel 3, '11' on second wheel 4. Actuator 8, during the actuation stroke, applies spring load to the spring, adding to existing preload on the spring applied during device assembly, the preload on the spring applied during assembly being present in the spring while the actuator is in an original or starting position.

The indicator apparatus will continue to move during each successive actuation/operation by decrementing the first wheel from '9' to '0'. The second wheel driver tooth 14 on the first wheel 3 will not come into contact with the stud 9 on the base for the next ten actuations/operations. As a result, the second wheel 4 will continue to display '11' until the next "10$^{th}$" actuation is reached.

The indicator apparatus 1 will continue to operate in this manner until it reaches the count of zero. At this stage the shutter present on the second wheel will be displayed in the window region closing the window region off. The shutter may be printed imprinted, carved, etched, pasted, burned, or embossed to provide visual information in the form of numbers, words, letters, colors, pictograms or similar to indicate 'end of life' of the medicament product. Some exemplary text to indicate 'end of life' can include but may not be limited to '000', 'XXX', 'End', 'Replace', 'Exhausted', 'Empty', 'Refill', etc. (not shown).

Exemplary Aspects of the Invention

The following is a non-limiting list of exemplary aspects of the invention, which is intended to highlight some of the various embodiments of the invention.

1. An event-related status indicator apparatus comprising:
   a. a first indicator wheel comprising a first set of readable event indicators on one face and a second indicator wheel comprising a second set of readable event indicators on one face, the first and second set of indicators together or individually providing readable information concerning the current event status;

b. an actuator that causes the first wheel to move upon the occurrence of each registerable event such that the indicator in the first set of indicators reflecting the current event status changes to reflect the occurrence of the event;

c. a first positioning element and a second positioning element;

d. a first repositionable engagement unit and a second repositionable engagement unit, the first repositionable engagement unit engaging the second indicator wheel until it comes in contact with the first positioning element and the second repositionable engagement unit only engaging the second wheel when the second repositionable engagement unit engages the second positioning element; and e. optionally one or more status identifiers that identify which of the first set of indicators and which of the second set of indicators reflects the current event status, wherein, upon a set number of events, the first positioning element repositions the first repositionable engagement unit to release the second wheel, and substantially simultaneously, the second positioning element engages the second repositionable engagement unit to cause the second wheel to rotate to a position such that the indicator in the second set of indicators identified by the one or more status identifiers changes.

2. The indicator apparatus according to Aspect 1, wherein the first wheel and the second wheel rotate about a common longitudinal axis of rotation and are oriented in the same direction.

3. The indicator apparatus according to any one of Aspects 1 or 2, wherein the indicator apparatus further comprises a base that contributes to maintaining the first wheel and the second wheel in position during operation.

4. The indicator apparatus according to Aspect 3, wherein the first repositionable engagement unit and the second positioning element are attached to, or are elements of, the base.

5. The indicator apparatus according to any one of Aspects 1-4, wherein the first positioning element and the second repositionable engagement unit are attached to, or are elements of, the first wheel.

6. The indicator apparatus according to any one of Aspects 1-5, wherein the first wheel comprises a latching mechanism that can be releasably engaged by the actuator such that when engaged by the actuator, the actuator can move the first wheel.

7. The indicator apparatus according to any one of Aspects 1-6, wherein the second wheel comprises a latching mechanism that the second repositionable engagement unit releasably engages when the second repositionable engagement unit comes in contact with the second positioning element to cause the second wheel to move when released.

8. The indicator apparatus according to Aspect 7, wherein the apparatus comprises (a) a latching mechanism on the first wheel that comprises a first set of teeth, (b) a latching mechanism on the second wheel that comprises a second set of teeth, or (c) latching mechanisms on both the first and second wheel that each comprise a set of teeth.

9. The indicator apparatus according to any one of Aspects 1-8, wherein the first and second repositionable engagement units are elongated members, each elongated member being fixed (immobile) on a first end and movable on a second end, the second end of the first repositionable engagement unit capable of being in an second wheel stabilizing position and a second wheel non-stabilizing position, the second end of the second repositionable engagement unit capable of being in an engaged position and an non-engaged position with the second wheel and wherein (i) when the first repositionable engagement unit is in a stabilizing position, the second repositionable engagement unit is in a non-engaged position and (ii) when the first repositionable engagement unit is in a non-stabilizing position, the second repositionable engagement unit is in an engaged position.

10. The indicator apparatus according to Aspect 9, wherein the first repositionable engagement unit is a stabilizing arm capable of being in a stabilizing position or a non-stabilizing position relative to the second wheel latching mechanism.

11. The indicator apparatus according to any one of Aspects 9-10, wherein the second repositionable engagement unit is a drive arm capable of being in an engaged or non-engaged position relative to the second wheel latching mechanism.

12. The indicator apparatus according to any one of Aspects 1-11, wherein the first positioning element is a deflector capable of modifying the position of the first repositionable engagement unit from a stabilizing position to a non-stabilizing position relative to the second wheel latching mechanism.

13. The indicator apparatus according to any one of Aspects 1-12, wherein the second positioning element is a deflector capable of modifying the position of the second repositionable engagement unit from a non-engaged position to an engaged position relative to the second wheel latching mechanism.

14. The indicator apparatus according to any one of Aspects 1-13, wherein the actuator is a movable, mechanical element comprising a member to receive an actuation trigger associated with an event and a member to transfer the energy from the received actuation trigger to the first wheel.

15. The indicator apparatus according to Aspect 14, wherein the member of the actuator which receives an actuation energy is a boss or pin.

16. The indicator apparatus according to Aspect 14, wherein the transfer portion is an actuator pawl.

17. The indicator apparatus according to any one of Aspects 14-16, wherein the actuation trigger is received by the actuator as rectilinear motion and the actuator translates that trigger into a rotational motion.

18. The indicator apparatus according to any one of Aspects 14-17, wherein in response to the actuation trigger, the actuator moves in a linear direction along an axis offset to the longitudinal axis upon which the first and second wheels rotate.

19. The indicator apparatus according to any one of Aspects 3-18, wherein the first wheel and second wheel are located at least partially within the base such that the first wheel and second wheel are rotatable about the common longitudinal axis of rotation.

20. The indicator apparatus according to any one of Aspects 1-19, wherein the faces of the first and second wheels 1) each comprise a set of readable event indicators, and 2) are essentially coplanar and oriented in the same direction.

21. The indicator apparatus according to any one of Aspects 19-20, wherein the face of the first wheel comprising a set of event indicators lies within the outer diameter of the second wheel.

22. The indicator apparatus according to any one of Aspects 1-21, wherein the first repositionable engagement unit is a stabilizing arm attached to the base and the first positioning element is a deflector on the first wheel, wherein the stabilizing arm engages the second latching mechanism on the second wheel except when the stabilizer release engages the second latching arm, wherein the stabilizer release engages the second latching arm after the set number of events.

23. The indicator apparatus according to Aspect 22, wherein the set number of events is equal to ten, such that the second wheel moves with every tenth movement of the first wheel.

24. The indicator apparatus according to any one of Aspects 1-23, wherein the first set of indicators comprise a single numerical digit, and the second set of indicators comprises one or more numerical digits, such that the two sets of indicators combine to create a single number larger in magnitude than either the first or second set of indicators alone, the single number providing a count of either the number of events having been registered by the indicator apparatus or the number of events remaining in the life cycle of the indicator apparatus.

25. The indicator apparatus according to any one of Aspects 1-24, wherein the counter apparatus further comprises an element to automatically return the actuator to a starting position after release of the actuation trigger.

26. The indicator apparatus according to Aspect 25 wherein the actuator return element is a spring.

27. The indicator apparatus according to Aspect 16, wherein the first wheel comprises teeth that are ratchet teeth which engage with a catch element on the actuator pawl having a complementary ratchet design.

28. The indicator apparatus according to aspect 27, wherein the ratchet teeth of the first wheel and the ratchet design of the catch element on the actuator pawl cooperate to aid in preventing the reverse rotation of the first wheel.

29. The indicator apparatus according to any one of Aspects 1-28, wherein the second repositionable engagement unit comprises a driver catch which engages the second wheel latching mechanism when the second repositionable engagement unit is in the engaged position but not when the second repositionable engagement unit is in the non-engaged position.

30. The indicator apparatus according to any one of Aspects 1-29, wherein the first repositionable engagement unit comprises a stabilizer deflector to cooperate with the first positioning element to disengage the first repositionable engagement unit from the second wheel.

31. The indicator apparatus according to any one of Aspects 1-30, wherein the first repositionable engagement unit comprises a stabilizer catch to engage with the second wheel when the first repositionable engagement unit is in a stabilizing position.

32. The indicator apparatus according to any one of Aspects 1-31, wherein the counter apparatus is housed within a product dosing dispenser.

33. The indicator apparatus according to Aspect 32, wherein the indicators indicate how many applications of the product have been administered or remain available for use.

34. The indicator apparatus according to any one of Aspects 32-33, wherein the dosing dispenser is a medicine dispenser.

35. The indicator apparatus according to Aspect 3433, wherein the medicine dispenser is a metered dose inhaler.

36. The indicator apparatus according to any one of Aspects 1-35, wherein the indicator apparatus cannot be reset to an initial event count upon reaching the end of its life cycle.

37. A dose dispenser having a dispenser body housing comprising:
   a. a container holding a substance or formulation to be dispensed, and
   b. the indicator apparatus according to any one of Aspects 1-36.

38. The dose dispenser according to Aspect 37, wherein the dose dispenser is a medicine dispenser.

39. The dose dispenser according to Aspect 38, wherein the medicine dispenser is a metered dose inhaler.

40. The dose dispenser according to any one of Aspects 37-39, wherein the container holding a substance or formulation to be dispensed is a pressurized aerosol canister.

41. The dose dispenser according to any one of Aspects 37-40, wherein the dispenser body further comprises a status identifier that identifies which of the first set of indicators and which of the second set of indicators of the indicator apparatus housed therein reflects the current event status.

42. The dose dispenser according to Aspect 41, wherein the status identifier is a viewing window in the dispenser body housing for viewing the visual message displayed by the indicator apparatus housed therein.

43. An event-related status indicator apparatus comprising:
   a. a first wheel and a second wheel each comprising indicator means for, together or individually, providing interpretable information concerning the current event status;
   b. a first positioning element and a second positioning element;
   c. a first means for movably engaging with the second wheel to stabilize the second wheel, and a second means for movably engaging with the second wheel to drive rotation of the second wheel, and
   d. optionally one or more status identifiers that identify which of the first set of indicators and which of the second set of indicators reflects the current event status;
   wherein, upon a set number of events, the first positioning element repositions the first means for movably engaging with the second wheel, and substantially simultaneously, the second positioning element engages the second means for movably engaging with the second wheel to cause the second wheel to rotate to a position such that the indicator means on the second wheel identified by the one or more status identifiers changes, and
   e. an actuation means for receiving an actuation trigger event and causing the first wheel to move upon the occurrence of each actuation trigger event unless prevented from doing so by the event-related status indicator being at the end of its life cycle;

the first and second means of engagement operating such that when the first means is engaged the second wheel is non-rotatable and the second means is not engaged to drive rotation of the second wheel; and when the first means is non-engaged the second wheel is free to rotate and the second means is engaged so as to drive rotation of the second wheel.

44. The indicator apparatus of Aspect 43, wherein the indicator means is a means for counting the number of events having occurred or which remain in the life cycle of the indicator apparatus.

45. The indicator apparatus of any one of Aspects 43-44, wherein the first means for movably engaging with the second wheel is a latching means of engaging with a second wheel latching mechanism.

46. The indicator apparatus of any one of Aspects 43-45, wherein the second means for movably engaging with the second wheel is a latching means of engaging with the second wheel latching mechanism.

47. The indicator apparatus of any one of Aspects 43-46, wherein the actuator means is a means of receiving energy from an actuation trigger event and transferring the energy from the actuation trigger event to the first wheel by latchingly engaging the first wheel.

The invention claimed is:

1. An event-related status indicator apparatus comprising:
   a. a first indicator wheel comprising a first set of readable event indicators on one face and a second indicator wheel comprising a second set of readable event indicators on one face, the first and second set of indicators together or individually providing readable information concerning a current event status;
   b. an actuator that causes the first wheel to move upon an occurrence of each registerable event such that an indicator in the first set of indicators reflecting the current event status changes to reflect the occurrence of the event;
   c. a first positioning element and a second positioning element; and
   d. a first repositionable engagement unit and a second repositionable engagement unit, the first repositionable engagement unit engaging the second indicator wheel until the first repositionable engagement unit comes in contact with the first positioning element and the second repositionable engagement unit only engaging the second wheel when the second repositionable engagement unit engages the second positioning element;
   wherein, upon a set number of events, the first positioning element repositions the first repositionable engagement unit to release the second wheel, and substantially simultaneously, the second positioning element engages the second repositionable engagement unit to cause the second wheel to rotate to a position such that the indicator in the second set of indicators changes.

2. The indicator apparatus according to claim 1, wherein the first wheel and the second wheel rotate about a common longitudinal axis of rotation and are oriented in the same direction.

3. The indicator apparatus according to claim 1, wherein the indicator apparatus further comprises a base that contributes to maintaining the first wheel and the second wheel in position during operation.

4. The indicator apparatus according to claim 3, wherein the first repositionable engagement unit and the second positioning element are attached to, or are elements of, the base.

5. The indicator apparatus according to claim 1, wherein the first positioning element and the second repositionable engagement unit are attached to, or are elements of, the first wheel.

6. The indicator apparatus according to claim 1, wherein the first wheel comprises a latching mechanism that can be releasably engaged by the actuator such that when engaged by the actuator, the actuator can move the first wheel.

7. The indicator apparatus according to claim 1, wherein the second wheel comprises a latching mechanism that the second repositionable engagement unit releasably engages when the second repositionable engagement unit comes in contact with the second positioning element to cause the second wheel to move when released.

8. The indicator apparatus according to claim 1, wherein the apparatus comprises (a) a latching mechanism on the first wheel that comprises a first set of teeth, (b) a latching mechanism on the second wheel that comprises a second set of teeth, or (c) latching mechanisms on both the first and second wheel that each comprise a set of teeth.

9. The indicator apparatus according to claim 1, wherein the first and second repositionable engagement units are elongated members, each elongated member being fixed (immobile) on a first end and movable on a second end, the second end of the first repositionable engagement unit capable of being in an second wheel stabilizing position and a second wheel non-stabilizing position, the second end of the second repositionable engagement unit capable of being in an engaged position and an non-engaged position with the second wheel and wherein (i) when the first repositionable engagement unit is in a stabilizing position, the second repositionable engagement unit is in a non-engaged position and (ii) when the first repositionable engagement unit is in a non-stabilizing position, the second repositionable engagement unit is in an engaged position.

10. The indicator apparatus according to claim 9, wherein the first repositionable engagement unit is a stabilizing arm capable of being in a stabilizing position or a non stabilizing position relative to the second wheel latching mechanism.

11. The indicator apparatus according to claim 9, wherein the second repositionable engagement unit is a drive arm capable of being in an engaged or non-engaged position relative to the second wheel latching mechanism.

12. The indicator apparatus according to claim 1, wherein the first positioning element is a deflector capable of modifying a position of the first repositionable engagement unit from a stabilizing position to a non-stabilizing position relative to the second wheel latching mechanism.

13. The indicator apparatus according to claim 1, wherein the second positioning element is a deflector capable of modifying a position of the second repositionable engagement unit from a non-engaged position to an engaged position relative to the second wheel latching mechanism.

14. The indicator apparatus according to claim 1, wherein the actuator is a movable, mechanical element comprising a member to receive an actuation trigger associated with an event and a member to transfer the energy from the received actuation trigger to the first wheel.

15. The indicator apparatus according to claim 14, wherein the member of the actuator which receives an actuation energy is a boss or pin.

16. The indicator apparatus according to claim 14, wherein the member to transfer the energy is an actuator pawl.

17. The indicator apparatus according to claim 14, wherein the actuation trigger is received by the actuator as rectilinear motion and the actuator translates that trigger into a rotational motion.

18. The indicator apparatus according to claim 14, wherein in response to the actuation trigger, the actuator moves in a linear direction along an axis offset to the longitudinal axis upon which the first and second wheels rotate.

19. The indicator apparatus according to claim 3, wherein the first wheel and second wheel are located at least partially within the base such that the first wheel and second wheel are rotatable about the common longitudinal axis of rotation.

20. The indicator apparatus according to claim 1, wherein the faces of the first and second wheels 1) each comprise a set of readable event indicators, and 2) are essentially coplanar and oriented in the same direction.

21. The indicator apparatus according to claim 20, wherein the face of the first wheel comprising a set of event indicators lies within the outer diameter of the second wheel.

22. The indicator apparatus according to claim 1, wherein the first repositionable engagement unit is a stabilizing arm attached to the base and the first positioning element is a deflector on the first wheel, wherein the stabilizing arm engages the second wheel latching mechanism except when the deflector release engages the second wheel latching mechanism, wherein the deflector release engages the second wheel latching mechanism after the set number of events.

23. The indicator apparatus according to claim 22, wherein the set number of events is equal to ten, such that the second wheel moves with every tenth movement of the first wheel.

24. The indicator apparatus according to claim 1, wherein the first set of indicators comprise a single numerical digit, and the second set of indicators comprises one or more numerical digits, such that the two sets of indicators combine to create a single number larger in magnitude than either the first or second set of indicators alone, the single number providing a count of either the number of events having been registered by the indicator apparatus or the number of events remaining in the life cycle of the indicator apparatus.

25. The indicator apparatus according to claim 1, wherein the indicator apparatus further comprises an element to automatically return the actuator to a starting position after release of the actuation trigger.

26. The indicator apparatus according to claim 25 wherein the actuator return element is a spring.

27. The indicator apparatus according to claim 16, wherein the first wheel comprises teeth that are ratchet teeth which engage with a catch element on the actuator pawl having a complementary ratchet design.

28. The indicator apparatus according to claim 27, wherein the ratchet teeth of the first wheel and the ratchet design of the catch element on the actuator pawl cooperate to aid in preventing the reverse rotation of the first wheel.

29. The indicator apparatus according to claim 1, wherein the second repositionable engagement unit comprises a driver catch which engages the second wheel latching mechanism when the second repositionable engagement unit is in the engaged position but not when the second repositionable engagement unit is in the non-engaged position.

30. The indicator apparatus according to claim 1, wherein the first repositionable engagement unit comprises a stabilizer deflector to cooperate with the first positioning element to disengage the first repositionable engagement unit from the second wheel.

31. The indicator apparatus according to claim 1, wherein the first repositionable engagement unit comprises a stabilizer catch to engage with the second wheel when the first repositionable engagement unit is in a stabilizing position.

32. A dose dispenser having a dispenser body housing comprising: a. a container holding a substance or formulation to be dispensed, and b. the indicator apparatus according to claim 1.

33. The dose dispenser according to claim 32, wherein the container holding a substance or formulation to be dispensed is a pressurized aerosol canister.

34. The dose dispenser according to claim 32, wherein the dispenser body further comprises a status identifier that identifies which of the first set of indicators and which of the second set of indicators of the indicator apparatus housed therein reflects the current event status.

35. The dose dispenser according to claim 34, wherein the status identifier is a viewing window in the dispenser body housing for viewing the visual message displayed by the indicator apparatus housed therein.

* * * * *